United States Patent [19]
Vandenburgh

[11] Patent Number: 5,869,041
[45] Date of Patent: Feb. 9, 1999

[54] DELIVERY OF BIOACTIVE COMPOUNDS TO AN ORGANISM

[75] Inventor: Herman H. Vandenburgh, Providence, R.I.

[73] Assignee: The Miriam Hospital, Providence, R.I.

[21] Appl. No.: 712,111

[22] Filed: Sep. 13, 1996

Related U.S. Application Data

[63] Continuation-in-part of Ser. No. 587,376, Jan. 12, 1996, abandoned.

[51] Int. Cl.$^6$ .............................. A61K 48/00; C12N 5/00
[52] U.S. Cl. ...................... 424/93.21; 435/325; 435/366; 435/373; 435/391
[58] Field of Search .................................. 435/325, 373, 435/377; 424/93.1, 93.2, 93.21; 514/44

[56] References Cited

U.S. PATENT DOCUMENTS

| | | |
|---|---|---|
| 5,164,368 | 11/1992 | Recker . |
| 5,399,677 | 3/1995 | Wolfman et al. . |

FOREIGN PATENT DOCUMENTS

| | | |
|---|---|---|
| WO 90/11366 | 10/1990 | WIPO . |
| WO 93/03768 | 3/1993 | WIPO . |
| WO 93/05751 | 4/1993 | WIPO . |
| WO 93/09222 | 5/1993 | WIPO . |
| WO 93/09229 | 5/1993 | WIPO . |
| WO93/00439 | 10/1993 | WIPO . |
| WO93/21859 | 11/1993 | WIPO . |
| WO 95/11983 | 5/1995 | WIPO . |
| WO 95/27518 | 10/1995 | WIPO . |
| WO 96/18303 | 6/1996 | WIPO . |

OTHER PUBLICATIONS

Ahrens, M., et al., Expression of Human Bone Morphogenetic Proteins–2 or –4 in Murine Mesenchymal Progenitor C3H10T1/2 Cells Induces Differentiation into Distinct Mesenchymal Cell Lineages, DNA and Cell Bio., 12:871–880 (1993).

Fang, J., et al., Stimulation of new bone formation by direct transfer of osteogenic plasmid genes, Proc. Natl. Acad. Sci., 93:5753–5758 (1996).

Fujimura, K., et al., Experimental Studies on Bone Inducing Activity of Composites of Atelopeptide Type I Collagen as Carrier for Ectopic Osteoinduction by rhBMP–2, Biochemical and Biophysical Res. Comm., 208:316–322 (1995).

Isobe, M., et al., Bone morphogenetic protein encapsulated with a biodegradable and biocompatible polymer, J. of Biomed. Mat. Res., 32:433–438 (1996).

Israel, D.J., Expression and Characterization of Bone Morphogenetic Protein–2 in Chinese Hamster Ovary Cells, Growth Factors, 7:139–150 (1992).

Kenley, R., et al., Osseous regeneration in the rat calvarium using novel delivery systems for recombinant human bone morphogenetic protein–2 (rhBMP–2), J. Biomed. Mat. Res., 28:1139–1147 (1994).

Kirker–Head, C.A., et al., Long–Term Healing of Bone Using Recombinant Human Bone Morphogenetic Protein 2, Clin. Orthopaedics and Related Res., 318:222–230 (1995).

Lee, S.C., Healing of large segmental defects in rat femurs is aided by RhBMP–2 in PLGA matrix, J. Biomed. Mat. Res., 28:1149–1156 (1994).

Marden, L.J., Recombinant human bone morphogenetic protein–2 is superior to demineralized bone matrix in repairing craniotomy defects in rats, J. Biomed. Mat. Res., 28:1127–1138 (1994).

Muschler, G.F., M.D., et al., Evaluation of Human Bone Morphogenetic Protein 2 in a Canine Spinal Fusion Model, Clin. Orthopaedics and Related Res., 308:229–240 (1994).

Ohgushi, H., In vitro bone formation by rat marrow cell culture, J. of Biomed. Mat. Res., 32:333–340 (1996).

Volek–Smith, H., et al., Recombinant Human Bone Morphogenetic Protein (rhBMP) Induced Heterotopic Bone Development In Vivo and In Vitro, Proc. Soc. Expt. Biol. Med., 211:265–272 (1995).

Wang, E.A., et al., Bone Morphogenetic Protein–2 Causes Commitment and Differentiation in C3H101T1/2 and 3T3 Cells, Growth Factors, 9:57–71 (1993).

Wozney, J.M., Novel Regulators of Bone Formation: Molecular Clones and Activities, Science, 242:1528–1534 (1988).

Perrone, Fenwich–Smith and Vandenburgh, Collagen and Stretch Modulate Autocrine Secretion of Insulin–like Growth Factor–1 and Insuline–like Growth Factor Binding Proteins from Differentiated Skeletal Muscle Cells, Nov. 7, 1994, The Journal of Biological Chemistry.

*Primary Examiner*—Deborah Crouch
*Attorney, Agent, or Firm*—Banner & Witcoff, Ltd.

[57] ABSTRACT

Disclosed herein is a method of delivering a bioactive compound to an organism that involves growing individual cells in vitro under conditions that allow the formation of an organized tissue, at least a subset of the cells containing a foreign DNA sequence which mediates the production of the bioactive compound; and implanting the organized tissue into the organism, whereby the bioactive compound is produced and delivered to the organism. Also disclosed herein is an in vitro method for producing a tissue having in vivo-like gross and cellular morphology that involves providing precursor cells of the tissue; mixing the cells with a solution of extracellular matrix components to create a suspension; placing the suspension in a vessel having a three dimensional geometry approximating the in vivo gross and cellular morphology of the tissue and having attachment surfaces coupled thereto; allowing the suspension to coalesce; and culturing the cells under conditions in which the cells form an organized tissue connected to the attachment surfaces. Also disclosed herein is an apparatus for producing in vitro a tissue having in vivo-like gross and cellular morphology. This apparatus includes a vessel having a three dimensional geometry approximating the in vivo morphology of the tissue and tissue attachment surfaces coupled thereto.

36 Claims, 12 Drawing Sheets

| CELL TYPE | N | ALKALINE PHOSPHATASE ACTIVITY (μg/h/mg CELLULAR PROTEIN) (MEAN ± ST. ERR.) | TOTAL CELLULAR PROTEIN (mg) (MEAN ± ST. ERR.) |
|---|---|---|---|
| $C_2C_{12}$ CELLS | 4 | 1.21 ± 0.02 | 0.391 ± 0.019 |
| $C_2$-LXSN CELLS | 4 | 1.15 ± 0.07 | 0.413 ± 0.018 |
| $C_2$-BMP6 CELLS | 4 | 2.79 ± 0.07 | 0.381 ± 0.016 |

DELIVERY OF BIOACTIVE COMPOUNDS TO AN ORGANISM

This application is a continuation-in-part of U.S. Ser. No. 08/587,376, filed Jan. 12, 1996, abandoned.

BACKGROUND OF THE INVENTION

This invention relates to the delivery of bioactive compounds to an organism, and in particular to methods and apparatus for the delivery of bioactive compounds by implanting into the organism an organized tissue producing the compounds.

One of the primary therapies used to treat disease is the delivery of bioactive compounds to the affected organism. Bioactive compounds may be delivered systemically or locally by a wide of variety of methods. For example, an exogenous source (i.e., produced outside the organism treated) of the bioactive compound may be provided intermittently by repeated doses. The route of administration may include oral consumption, injection, or tissue absorption via topical compositions, suppositories, inhalants, or the like. Exogenous sources of the bioactive compound may also be provided continuously over a defined time period. For example, delivery systems such as pumps, time-released compositions, or the like may be implanted into the organism on a semi-permanent basis for the administration of bioactive compounds (e.g., insulin, estrogen, progesterone, etc.).

The delivery of bioactive compounds from an endogenous source (i.e., produced within the organism treated) has also been attempted. Traditionally, this was accomplished by transplanting, from another organism, an organ or tissue whose normal physiological function was the production of the bioactive compound (e.g., liver transplantation, kidney transplantation, or the like). More recently, endogenous production by cells of the affected organism has been accomplished by inserting into the cells a DNA sequence which mediates the production of the bioactive compound. Commonly known as gene therapy, this method includes inserting the DNA sequence into the cells of the organism in vivo. The DNA sequence persists either transiently or permanently as an extra-chromosomal vector (e.g., when inserted by adenovirus infection or by direct injection of a plasmid) or integrates into the host cell genome (e.g., when inserted by retrovirus infection). Alternatively, the DNA sequence may be inserted into cells of the host tissue or an another organism in vitro, and the cells subsequently transplanted into the organism to be treated.

SUMMARY OF THE INVENTION

In general, the invention features a method of delivering a bioactive compound to an organism. The method includes the steps of growing a plurality of cells in vitro under conditions that allow the formation of an organized tissue, at least a subset of the cells containing a foreign DNA sequence which mediates the production of the bioactive compound, and implanting the cells into the organism, whereby the bioactive compound is produced and delivered to the organism.

In a preferred embodiment of this method, the step of growing may include mixing the cells with a solution of extracellular matrix components to create a suspension, placing the suspension in a vessel having a three-dimensional geometry approximating the in vivo gross morphology of the tissue and having tissue attachments surfaces thereon, allowing the suspension to coalesce, and culturing the coalesced suspension under conditions in which the cells connect to the attachment surfaces and form a tissue having an in vivo-like gross and cellular morphology.

In other preferred embodiments, the DNA sequence encodes the bioactive compound; the DNA sequence encodes a protein which mediates the production of the bioactive compound (for example, by regulating its expression or encoding an intermediate to the bioactive compound); the DNA sequence mediates the production of two bioactive compounds; the tissue includes skeletal muscle; the tissue includes myotubes; the bioactive compound is a growth factor (for example, human growth hormone); the bioactive compound is a bone morphogenetic protein; the bone morphogenetic protein is BMP-6; the organized tissue is implanted into the tissue of origin of at least one of the cells; the cells include a first and a second population of cells, at least a subset of each of the populations containing a foreign DNA sequence which mediates the production of a bioactive compound; the foreign DNA sequence of the first population mediates the production of a bioactive compound different from the foreign DNA sequence of the second population; and the foreign DNA sequence of the first population encodes a bone morphogenetic protein and the foreign DNA sequence of the second population includes a parathyroid hormone.

In other preferred embodiments, the method includes: the step of removing the organized tissue from the organism to terminate delivery of the bioactive compound; following the removal step, the step of culturing the organized tissue in vitro under conditions which preserve its in vivo viability; following the culturing step, the step of reimplanting the organized tissue into the organism to deliver the bioactive compound to the organism; the step of isolating primary cell types of at least one of the cell types of the tissue; and the step of utilizing immortalized cells of at least one of the cell types of the tissue.

In other preferred embodiments of this method, the tissue comprises substantially post-mitotic cells; during the growing step, a force is exerted substantially parallel to a dimension of the tissue; the force is exerted on the individual cells during growth in vitro and on the organized tissue during implantation in vivo; the coalesced suspension exerts a force on the cells substantially parallel to a dimension of the vessel; the cells are aligned substantially parallel to a dimension of the vessel; the vessel is substantially semi-cylindrical in shape; the attachment surfaces are positioned at opposite ends of the vessel; the alignment is mediated by forces exerted by the coalesced suspension; the cells comprise myotubes; the organism is a mammal; and the mammal is a human.

In a related aspect, the invention features an organized tissue producing a bioactive compound, the tissue is produced by the steps of mixing a plurality of cells with a solution of extracellular matrix components to create a suspension, at least a subset of the cells containing a foreign DNA sequence which mediates the production of a bioactive compound; placing the suspension in a vessel having a three dimensional geometry approximating the in vivo gross morphology of the tissue, the vessel having attachment surfaces thereon; allowing the suspension to coalesce; and culturing the coalesced suspension under conditions in which the cells connect to the attachment surfaces and form a tissue having an in vivo-like gross and cellular morphology.

In a related aspect, the invention features an organized tissue producing a bioactive compound. The organized tissue includes a plurality of cells, grown in vitro under conditions that allow the formation of an organized tissue, and a foreign DNA sequence mediating the production of a bioactive compound. The DNA sequence is inserted into at least a subset of the cells. Also included in the invention are organized tissues producing a bioactive compound, the tissue being produced by any of the methods described herein.

In preferred embodiments, the organized tissue is skeletal muscle.

In a related aspect, the invention features an in vitro method for producing a tissue having an in vivo-like gross and cellular morphology. The method includes providing precursor cells of the tissue; mixing the cells with a solution of extracellular matrix components to create a suspension; placing the suspension in a vessel having a three-dimensional geometry approximating the in vivo gross morphology of the tissue, the vessel having tissue attachment surfaces thereon; allowing the suspension to coalesce; and culturing the cells under conditions in which the cells form an organized tissue connected to the attachment surfaces.

In preferred embodiments of this method, the step of providing includes isolating primary cells of at least one of the cell types which make up the tissue or includes utilizing immortalized cells of at least one of the cell types which make up the tissue; the step of providing includes inserting a foreign DNA sequence into at least one of the cells which make up the tissue; the tissue includes substantially post-mitotic cells; the coalesced suspension exerts a force on the cells substantially parallel to a dimension of the vessel; the cells are aligned substantially parallel to a dimension of the vessel; the vessel is substantially semi-cylindrical in shape; and the attachment surfaces are positioned at opposite ends of the vessel.

In other preferred embodiments of this method, the DNA sequence encodes the bioactive compound; the DNA sequence encodes a protein which mediates the production of the bioactive compound; the DNA sequence mediates the production of two bioactive compounds; the bioactive compound is a growth factor; the organized tissue is implanted into the organism, whereby the bioactive compound is produced and delivered to the organism; and the organized tissue is implanted into the tissue of origin of at least one of the cells.

In a related aspect, the invention features an organized tissue produced by the steps of providing precursor cells of the tissue; mixing the cells with a solution of extracellular matrix components to create a suspension; placing the suspension in a vessel having a three-dimensional geometry approximating the in vivo gross morphology of the tissue, the vessel having tissue attachment surfaces thereon; allowing the suspension to coalesce; and culturing the cells under conditions in which the cells form an organized tissue connected to the attachment surfaces. Also included in the invention are organized tissues produced by any of the methods described herein.

In a related aspect, the invention features an apparatus for producing a tissue in vitro having an in vivo-like gross and cellular morphology. The apparatus includes a vessel having a three-dimensional geometry approximating the in vivo gross morphology of the tissue and having tissue attachment surfaces in the vessel.

In preferred embodiments of this aspect of the invention, the apparatus further includes a culture chamber in which the vessel may be submerged; the vessel is substantially semi-cylindrical in shape; the attachment surfaces are coupled to opposite ends of the semi-cylindrical vessel; the coalesced suspension exerts a force on the cells substantially parallel to a dimension of the vessel; and the cells are aligned substantially parallel to a dimension of the vessel.

In a related aspect, the invention features a method of regulating bone formation in an organism. The method includes the steps of growing a plurality of cells in vitro under conditions that allow the formation of an organized tissue, at least a subset of the cells containing a foreign DNA sequence which mediates the production of a bone morphogenetic protein, and implanting the tissue into the organism, whereby the bone morphogenetic protein is produced and delivered to chondroblastic or osteoblastic precursor cells.

In a preferred embodiment of this method, the step of growing may include mixing the cells with a solution of extracellular matrix components to create a suspension; placing the suspension in a vessel having a three-dimensional geometry approximating the in vivo gross morphology of the tissue and having tissue attachments surfaces thereon; allowing the suspension to coalesce; and culturing the coalesced suspension under conditions in which the cells connect to the attachment surfaces and form a tissue having an in vivo-like gross and cellular morphology.

In other preferred embodiments, the DNA sequence encodes the bone morphogenetic protein; the DNA sequence encodes BMP-6; the DNA sequence encodes a protein which mediates the production of the bone morphogenetic protein (for example, by regulating its expression or encoding an intermediate to the bioactive compound); the DNA sequence also mediates the production of another bioactive compound; the tissue includes skeletal muscle; the tissue includes myotubes; the bioactive compound is a growth factor (for example, human growth hormone); the organized tissue is implanted into the tissue of origin of at least one of the cells; the cells include a first and a second population of cells, at least a subset of each of the populations containing a foreign DNA sequence which mediates the production of a bioactive compound; the foreign DNA sequence of the first population mediates the production of a bioactive compound different from the foreign DNA sequence of the second population; and the foreign DNA sequence of the first population encodes a bone morphogenetic protein and the foreign DNA sequence of the second population includes a parathyroid hormone.

In other preferred embodiments, the method includes: the step of removing the organized tissue from the organism to terminate delivery of the bone morphogenetic protein; following the removal step, the step of culturing the organized tissue in vitro under conditions which preserve its in vivo viability; following the culturing step, the step of reimplanting the organized tissue into the organism to deliver the bone morphogenetic protein to the organism; the step of isolating primary cell types of at least one of the cell types of the tissue; and the step of utilizing immortalized cells of at least one of the cell types of the tissue.

In other preferred embodiments of this method, the tissue comprises substantially post-mitotic cells; during the growing step, a force is exerted substantially parallel to a dimension of the tissue; the force is exerted on the individual cells during growth in vitro and on the organized tissue during implantation in vivo; the coalesced suspension exerts a force on the cells substantially parallel to a dimension of the vessel; the cells are aligned substantially parallel to a dimension of the vessel; the vessel is substantially semi-cylindrical in shape; the attachment surfaces are positioned at opposite ends of the vessel; the alignment is mediated by forces exerted by the coalesced suspension; the cells comprise myotubes; the organism is a mammal; and the mammal is a human.

As used herein, by a "bioactive compound" is meant a compound which influences the biological structure, function, or activity of a cell or tissue of a living organism.

By "bone morphogenetic protein" is meant an extracellular osteogenic-stimulating molecule belonging to the TGF-β superfamily. Bone morphogenetic proteins ("BMP") include a large number of proteins, for example, BMP-2, -3, -4, -5, -6, -7, -11, and -12. Bone morphogenetic proteins control the cellular events associated with bone and cartilage formation and repair (e.g., cellular growth, proliferation, and differentiation). For example, bone morphogenetic proteins alter the differentiation pathway of mesenchymal cells towards the chondroblastic or osteoblastic lineage.

By "organized tissue" or "organoid" is meant a tissue formed in vitro from a collection of cells having a cellular organization and gross morphology similar to that of the tissue of origin for at least a subset of the cells in the collection. An organized tissue or organoid may include a mixture of different cells, for example, muscle, fibroblast, and nerve cells, but must exhibit the in vivo cellular organization and gross morphology of a tissue including at least one of those cells, for example, the organization and morphology of muscle tissue.

By "in vivo-like gross and cellular morphology" is meant a three-dimensional shape and cellular organization substantially similar to that of the tissue in vivo.

By "extracellular matrix components" is meant compounds, whether natural or synthetic compounds, which function as substrates for cell attachment and growth. Examples of extracellular matrix components include, without limitation, collagen, laminin, fibronectin, vitronectin, elastin, glycosaminoglycans, proteoglycans, and combinations of some or all of these components (e.g., Matrigel™, Collaborative Research, Catalog No. 40234).

By "tissue attachment surfaces" is meant surfaces having a texture, charge or coating to which cells may adhere in vitro. Examples of attachment surfaces include, without limitation, stainless steel wire, VELCRO™, suturing material, native tendon, covalently modified plastics (e.g., RGD complex), and silicon rubber tubing having a textured surface.

By "foreign DNA sequence" is meant a DNA sequence which differs from that of the wild type genomic DNA of the organism and may be extra-chromosomal, integrated into the chromosome, or the result of a mutation in the genomic DNA sequence.

By "substantially post-mitotic cells" is meant an organoid in which at least 50% of the cells containing a foreign DNA sequence are non-proliferative. Preferably, organoids including substantially post-mitotic cells are those in which at least 80% of the cells containing a foreign DNA sequence are non-proliferative. More preferably, organoids including substantially post-mitotic cells are those in which at least 90% of the cells containing a foreign DNA sequence are non-proliferative. Most preferably, organoids including substantially post-mitotic cells are those in which 99% of the cells containing a foreign DNA sequence are non-proliferative. Cells of an organoid retaining proliferative capacity may include cells of any of the types included in the tissue. For example, in skeletal muscle organoids, the proliferative cells may include muscle stem cells (i.e., satellite cells) and fibroblasts.

The invention provides a number of advantages. For example, implantation of an organized tissue produced in vitro provides quantifiable, reproducible, and localized delivery of bioactive compounds to an organism. Prior to implantation, the production of bioactive compounds by the organized tissue may be measured and quantified per unit time, per unit mass, or relative to any other physiologically-relevant parameter. In addition, the capability of an organized tissue to sustain production of bioactive compounds can be assessed by culturing for extended periods and assaying of compound production with time.

Moreover, because the organized tissue is implanted at a defined anatomical location as a discrete collection of cells, it may be distinguished from host tissues, removed post-implantation from the organism, and reimplanted into the organism at the same or a different location at the time of removal or following an interim period of culturing in vitro. This feature facilitates transient or localized delivery of the bioactive compound. Restriction of the cells producing bioactive compounds to particular anatomical sites also enhances the controlled delivery of bioactive compounds, especially where the organized tissue functions as a paracrine organ. The efficiency of delivery of a bioactive compound (i.e., the amount of the bioactive compound delivered to obtain a desired serum concentration) is also enhanced as compared to direct subcutaneous injection. Likewise, the efficiency of implanting post-mitotic cells containing a foreign DNA sequence into an organism (i.e., the number of cells in a post-mitotic state as a percentage of the initial number of cells containing the foreign DNA sequence) is enhanced by organoid implantation as compared to the implantation of individual mitotic cells. For example, skeletal muscle organoids produced in vitro include post-mitotic myofibers representing greater than 70% of the initial myoblasts containing a foreign DNA sequence, whereas direct implantation of the myoblasts results in post-mitotic myofibers representing less than 1% of the initial cells.

In addition, because substantially all of the implanted cells are fully differentiated, migration of these cells to other anatomical sites is reduced. Moreover, implantation of post-mitotic, non-migratory myofibers containing a foreign DNA reduces the possibility of cell transformation and tumor formation. The implantation of an organized tissue may even enhance the functional and structural characteristics of the host tissue.

Furthermore, because the method of producing a tissue having an in vivo-like gross and cellular morphology may be achieved without the application of external forces by mechanical devices, the apparatus for producing such a tissue is readily adaptable to standard cell and tissue culture systems. The apparatus and method may also be used to produce bone, cartilage, tendon, and cardiac tissues as these tissues include cell types which organize in response to external forces. In addition, the apparatus includes widely available, easily assembled and relatively inexpensive components.

Other advantages and features of the invention will be apparent from the detailed description, and from the claims.

DETAILED DESCRIPTION

Figure 1:
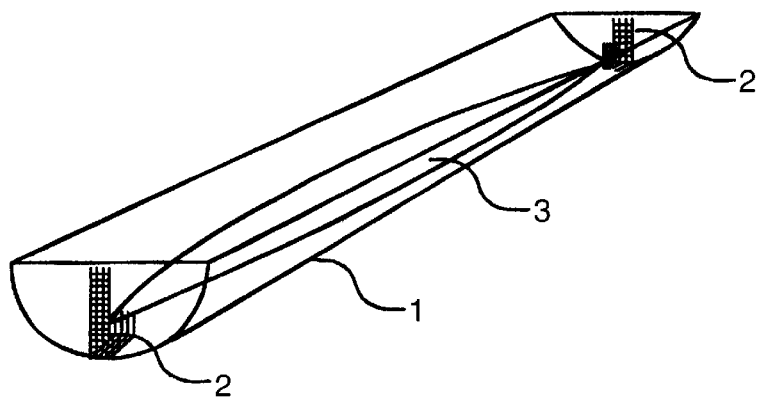
FIG. 1 is a diagram of a vessel for growing skeletal muscle tissue which will have an in vivo-like gross and cellular morphology.

I. In Vitro Production of Tissues Having In Vivo-like Gross and Cellular Morphology Organized tissues having in vivo-like gross and cellular morphology may be produced in vitro from the individual cells of a tissue of interest. As a first step in this process, disaggregated or partially disaggregated cells are mixed with a solution of extracellular matrix components to create a suspension. This suspension is then placed in a vessel having a three dimensional geometry which approximates the in vivo gross morphology of the tissue and includes tissue attachment surfaces coupled to the vessel. The cells and extracellular matrix components are then allowed to coalesce or gel within the vessel, and the vessel is placed within a culture chamber and surrounded with media under conditions in which the cells are allowed to form an organized tissue connected to the attachment surfaces.

Although this method is compatible with the in vitro production of a wide variety of tissues, it is particularly suitable for tissues in which at least a subset of the individual cells are exposed to and impacted by mechanical forces during tissue development, remodeling or normal physiologic function. Examples of such tissues include muscle, bone, skin, nerve, tendon, cartilage, connective tissue, endothelial tissue, epithelial tissue, and lung. More specific examples include skeletal, cardiac, and smooth muscle, stratified or lamellar bone, and hyaline cartilage. Where the tissue includes a plurality of cell types, the different types of cells may be obtained from the same or different organisms, the same or different donors, and the same or different tissues. Moreover, the cells may be primary cells or immortalized cells. Furthermore, all or some of the cells of the tissue may contain a foreign DNA sequence which mediates the production of a bioactive compound (as described herein).

The composition of the solution of extracellular matrix components will vary according to the tissue produced. Representative extracellular matrix components include, but are not limited to, collagen, laminin, fibronectin, vitronectin, elastin, glycosaminoglycans, proteoglycans, and combinations of some or all of these components (e.g., Matrigel™, Collaborative Research, Catalog No. 40234). In tissues containing cell types which are responsive to mechanical forces, the solution of extracellular matrix components preferably gels or coalesces such that the cells are exposed to forces associated with the internal tension in the gel.

Culture conditions will also vary according to the tissue produced. Methods for culturing cells are well known in the art and are described, for example, in *Animal Cell Culture: A Practical Approach,* (R. I. Fveshney, ed. IRL Press, 1986). In general, the vessel containing a coalesced suspension of cells and extracellular matrix components is placed in a standard culture chamber (e.g., wells, dishes, or the like), and the chamber is then filled with culture medium until the vessel is submerged. The composition of the culture medium is varied, for example, according to the tissue produced, the necessity of controlling the proliferation or differentiation of some or all of the cells in the tissue, the length of the culture period and the requirement for particular constituents to mediate the production of a particular bioactive compound. The culture vessel may be constructed from a variety of materials in a variety of shapes as described below.

An apparatus for producing a tissue in vitro having an in vivo-like gross and cellular morphology includes a vessel having a three dimensional geometry which approximates the in vivo gross morphology of the tissue. The apparatus also includes tissue attachment surfaces coupled to the vessel. Such a vessel may be constructed from a variety of materials which are compatible with the culturing of cells and tissues (e.g., capable of being sterilized and compatible with a particular solution of extracellular matrix components) and which are formable into three dimensional shapes approximating the in vivo gross morphology of a tissue of interest. The tissue attachment surfaces (e.g., stainless steel mesh, VELCRO™, or the like) are coupled to the vessel and positioned such that as the tissue forms in vitro the cells may adhere to and align between the attachment surfaces. The tissue attachment surfaces may be constructed from a variety of materials which are compatible with the culturing of cells and tissues (e.g., capable of being sterilized, or having an appropriate surface charge, texture, or coating for cell adherence).

The tissue attachment surfaces may be coupled in a variety of ways to an interior or exterior surface of the vessel. Alternatively, the tissue attachment surfaces may be coupled to the culture chamber such that they are positioned adjacent the vessel and accessible by the cells during tissue formation. In addition to serving as points of adherence, in certain tissue types (e.g., muscle), the attachment surfaces allow for the development of tension by the tissue between opposing attachment surfaces. Moreover, where it is desirable to maintain this tension in vivo, the tissue attachment surfaces may be implanted into an organism along with the tissue (see further discussion in Section II.).

One vessel according to the invention is shown in FIG. 1. This vessel 1, which is suitable for the in vitro production of a skeletal muscle organoid 3, has a substantially semi-cylindrical shape and tissue attachment surfaces 2 coupled to an interior surface of the vessel.

Figure 2:
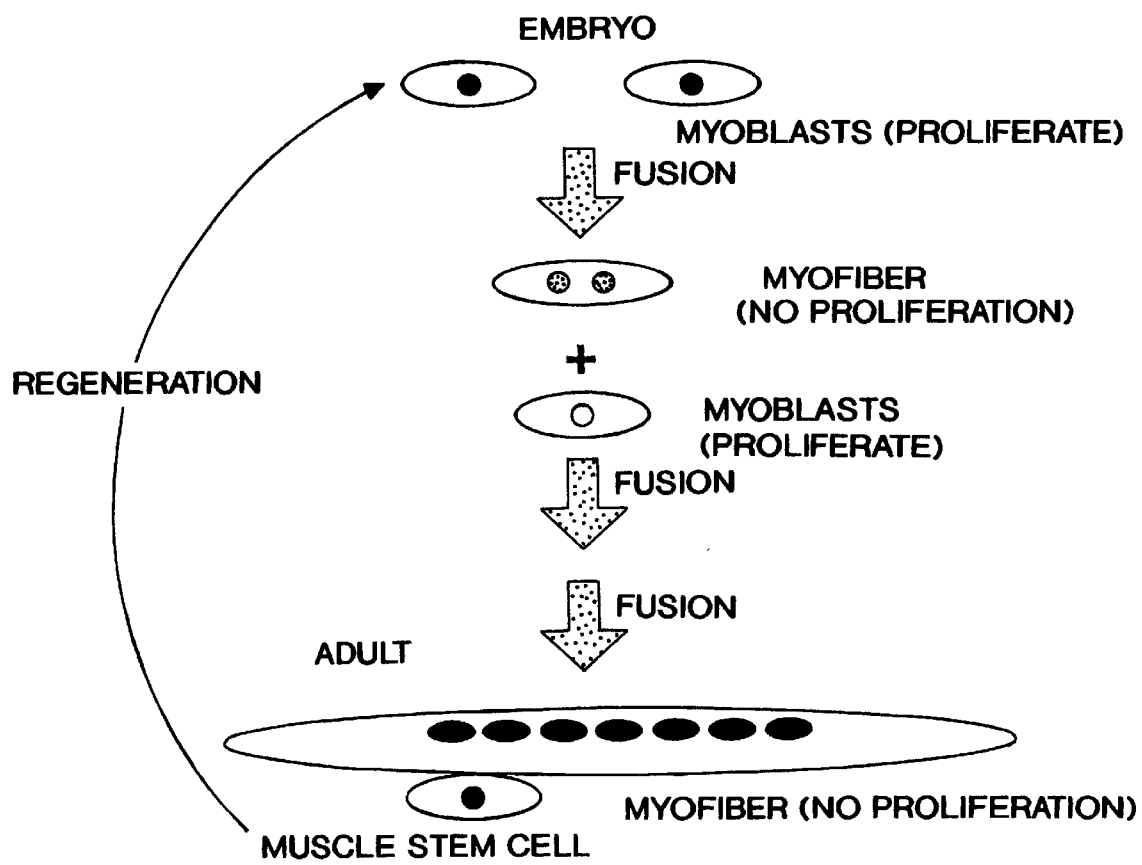
FIG. 2 is a flow chart of the process of skeletal muscle growth and regeneration.

A. In Vitro Production of a Skeletal Muscle Organoid having In Vivo-Like Gross and Cellular Morphology Using an apparatus and method as generally described above, a skeletal muscle organoid having an in vivo-like gross and cellular morphology was produced in vitro. An overview of the stages of skeletal muscle growth and regeneration is shown in FIG. 2. As shown, during skeletal muscle development embryonic myoblasts proliferate, differentiate, and then fuse to form multi-nucleated myofibers. Although the myofibers are non-proliferative, a population of muscle stem cells (i.e., satellite cells), derived from the embryonic myoblast precursor cells, retain their proliferative capacity and serve as a source of myoblasts for muscle regeneration in the adult organism. Therefore, either embryonic myoblasts or adult skeletal muscle stem cells may serve as one of the types of precursor cells for in vitro production of a skeletal muscle organoid.

To produce skeletal muscle cells capable of secreting a bioactive compound, primary rat or avian cells or immortalized murine cells secreting recombinant human growth hormone, were suspended in a solution of collagen and Matrigel™ which was maintained at 4° C. to prevent gelling. The cell suspension was then placed in a semi-cylindrical vessel with tissue attachment surfaces coupled to an interior surface at each end of the vessel. The vessel was positioned in the bottom of a standard cell culture chamber. Following two to four hours of incubation at 37° C., the gelled cell suspension was covered with fresh culture medium (renewed at 24 to 72 hour intervals) and the chamber containing the suspended cells was maintained in a humidified 5% $CO_2$ incubator at 37° C. throughout the experiment.

Between the second and sixth day of culture, the cells were found to be organized to the extent that they spontaneously detached from the vessel. At this stage, the cells were suspended in culture medium while coupled under tension between tissue attachment surfaces positioned at either end of the culture vessel. During the subsequent ten to fourteen days, the cells formed an organoid containing skeletal myofibers aligned parallel to each other in three dimensions. The alignment of the myofibers and the gross and cellular morphology of the organoid were similar to that of in vivo skeletal muscle.

To carry out the above method, an apparatus for organoid formation was constructed from silastic tubing and either VELCRO™ or metal screens as follows. A section of silastic tubing (approximately 5 mm I.D., 8 mm O.D., and 30 mm length) was split in half with a razor blade and sealed at each end with silicone rubber caulking. Strips of VELCRO™ (loop or hook side, 3 mm wide by 4 mm long) or L-shaped strips of stainless steel screen (3 mm wide by 4 mm long by 4 mm high) were then attached with silicone rubber caulking to the interior surface of the split tubing near the sealed ends. The apparatus was thoroughly rinsed with distilled/deionized water and subjected to gas sterilization.

Skeletal muscle organoids were produced in vitro from a C2C12 mouse skeletal muscle myoblast cell line stably co-transfected with recombinant human growth hormone-expressing and β-galactosidase-expressing (β-gal) constructs. Dhawan et al., *Science* 254:1509–1512, 1991. Cells were plated in the vessel at a density of 1–4×10$^6$ cells per vessel in 400 μl of a solution containing extracellular matrix components. The suspension of cells and extracellular matrix components was achieved by the following method. The solution includes 1 part Matrigel™ (Collaborative Research, Catalog No. 40234) and 6 parts of a 1.6 mg/ml solution of rat tail Type I collagen (Collaborative Research, Catalog No. 40236). The Matrigel™ was defrosted slowly on ice and kept chilled until use. The collagen solution was prepared just prior to cell plating by adding to lyophilized collagen, growth medium (see constituents below), and 0.1N NaOH in volumes equivalent to 90% and 10%, respectively, of the volume required to obtain a final concentration of 1.6 mg/ml and a pH of 7.0–7.3. The collagen, sodium hydroxide and growth medium were maintained on ice prior to and after mixing by inversion.

Freshly centrifuged cells were suspended in the collagen solution by trituration with a chilled sterile pipet. Matrigel™ was subsequently added with a chilled pipet and the suspension was once again mixed by trituration. The suspension of cells and extracellular matrix components was maintained on ice until it was plated in the vessel using chilled pipet tips. The solution was pipetted and spread along the length of the vessel, taking care to integrate the solution into the tissue attachment surfaces. The culture chamber containing the vessel was then placed in a standard cell culture incubator, taking care not to shake or disturb the suspension. The suspension was allowed to gel, and after 2 hours the culture chamber was filled with growth medium such that the vessel was submerged.

For a period of three days the cells were maintained on growth medium containing DMEM-high glucose (GIBCO-BRL), 5% fetal calf serum (Hyclone Laboratories), and 1% penicillin/streptomycin solution (final concentration 100 units/ml and 0.1 μg/ml, respectively). On the fourth day of culture, the cells were switched to fusion medium containing DMEM-high glucose, 2% horse serum (Hyclone Laboratories), and 100 units/ml penicillin for a period of 4 days. On the eighth day of culture, the cells were switched to maintenance medium containing DMEM-high glucose, 10% horse serum, 5% fetal calf serum, and 100 units/ml penicillin for the remainder of the experiment. Before the organoids were ready for implantation, some were cultured in maintenance media containing 1 μg/ml of cytosine arabinoside for the final four to eight days. Treatment with cytosine arabinoside eliminated proliferating cells and produced organoids including substantially post-mitotic cells.

Figure 3:
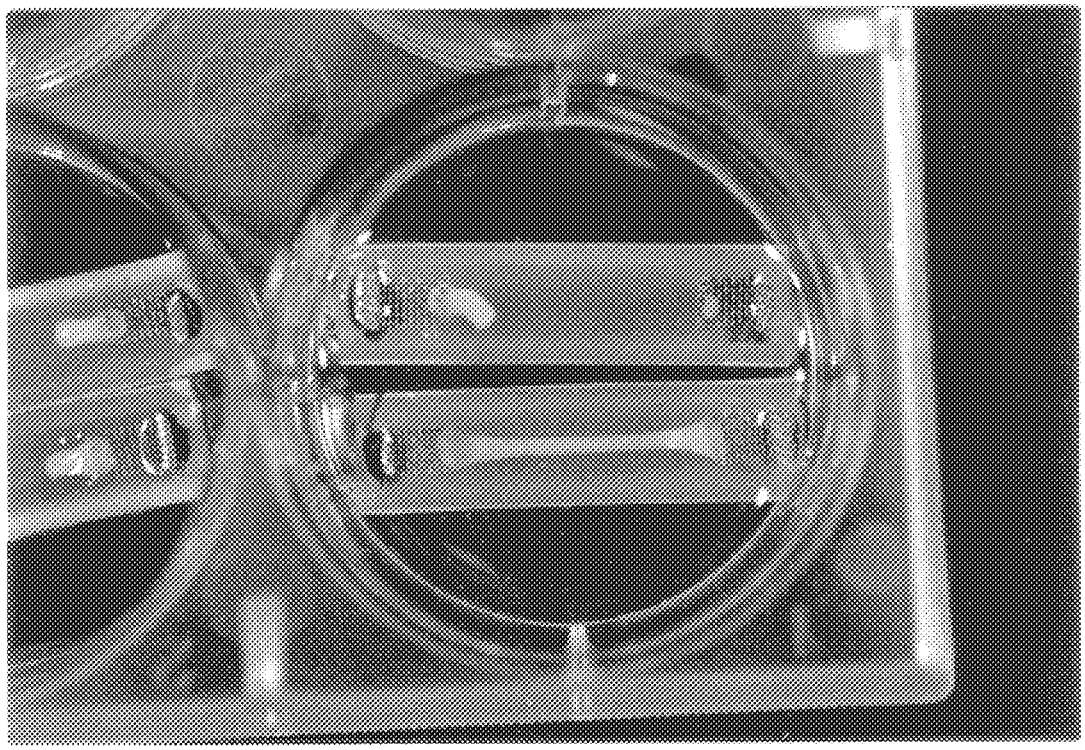
FIG. 3 is a photograph of skeletal muscle organoids formed in vitro from rhGH-secreting C2C12 cells.
Figure 4:
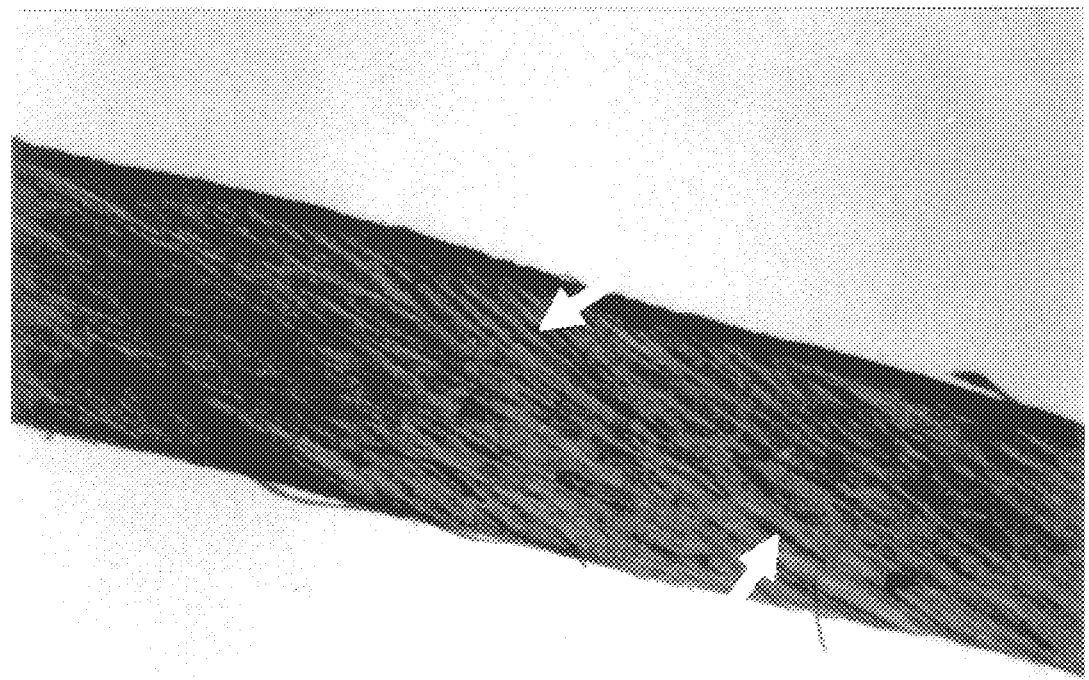
FIG. 4 is a micrograph of a section of a skeletal muscle organoid grown in vitro from rhGH-secreting C2C12 cells which has been stained for sarcomeric tropomyosin.
Figure 5:
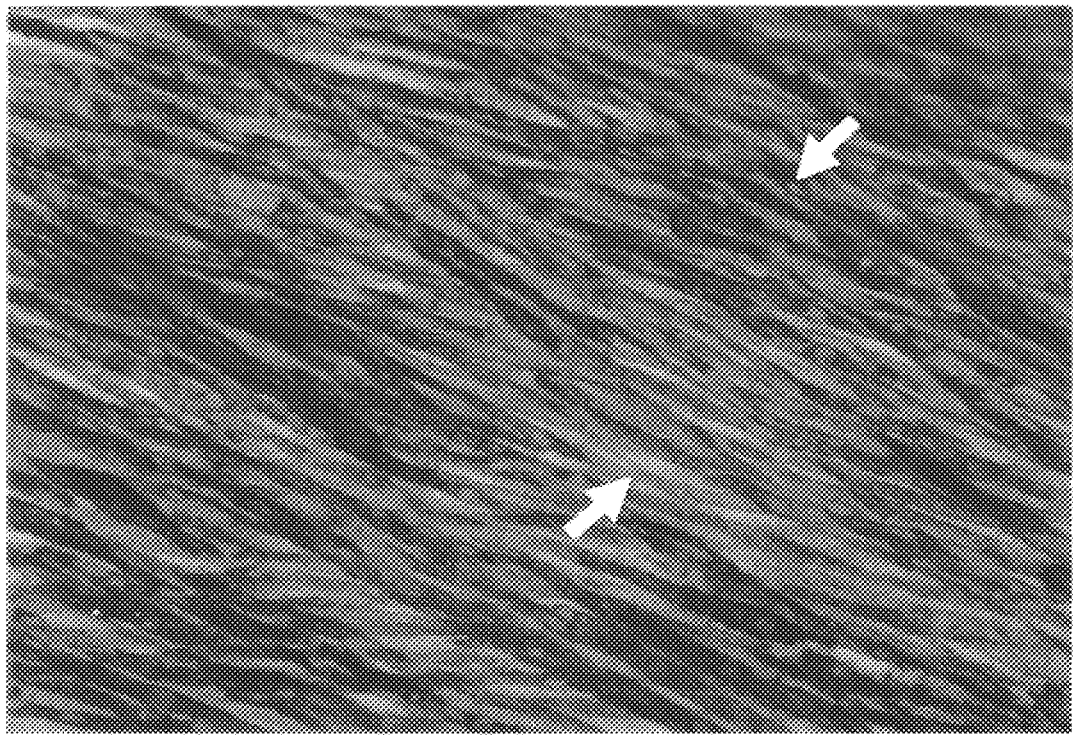
FIG. 5 is a micrograph of a section of a skeletal muscle organoid grown in vitro from rhGH-secreting C2C12 cells which has been stained for sarcomeric tropomyosin.
Figure 9A:
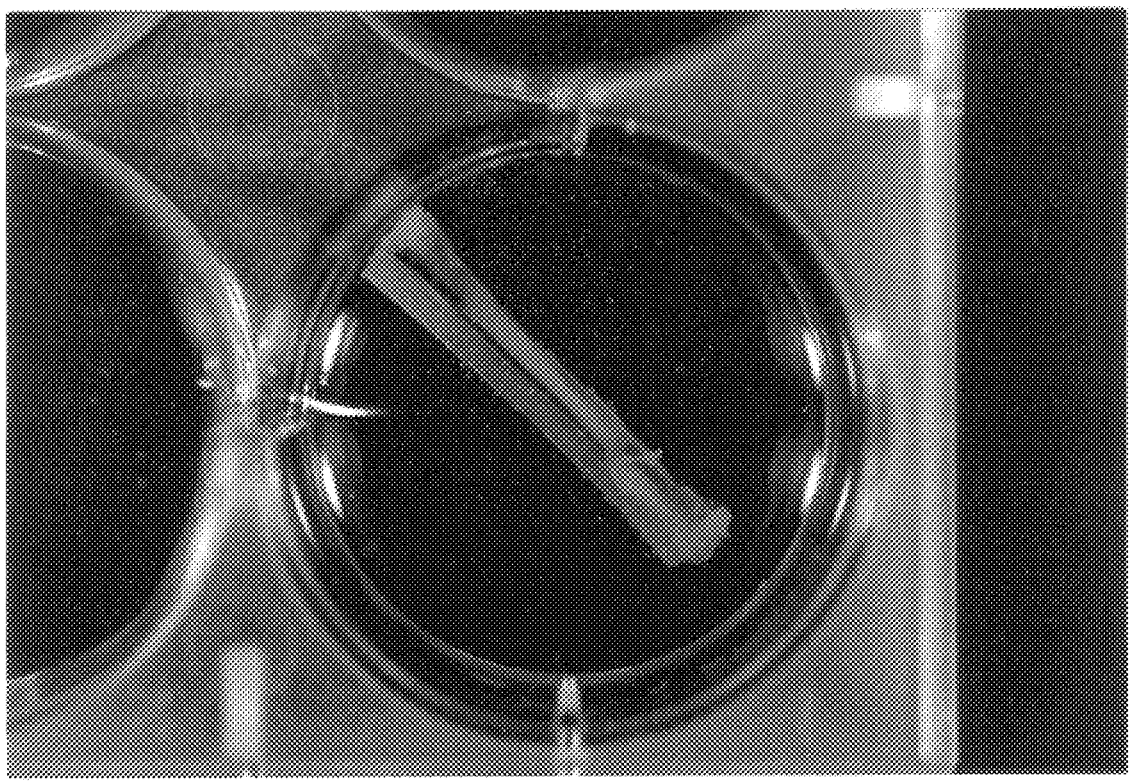
FIGS. 9A–9C are photographs of a skeletal muscle organoid grown in vitro from rhGH-secreting C2C12 cells, implanted in vivo, and subsequently removed and further cultured in vitro.
Figure 9B:
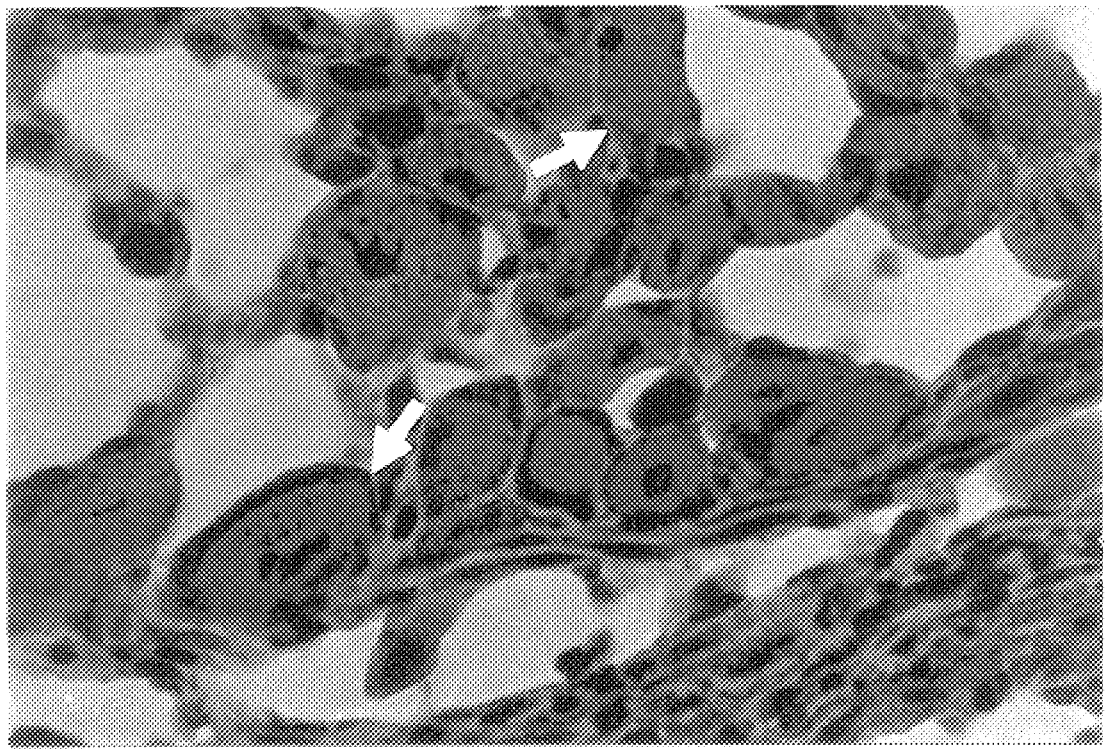

The cell-extracellular matrix gel (cell-gel) formed in vitro from these stably transfected C2C12 cells 48 hours after plating are shown in FIG. 3. In the upper half of the figure the cell-gel has detached from one of the tissue attachment surfaces. The resultant contraction demonstrates the tension developed in the gel between the tissue attachment surfaces. FIGS. 4 and 5 demonstrate the presence of a muscle-specific contractile protein (i.e., brown staining following incubation with an antibody to sarcomeric tropomyosin), in parallel arrays of highly organized and longitudinally oriented myofibers in mammalian skeletal muscle organoids following three weeks of culturing in the apparatus shown in FIG. 1. Moreover, FIG. 9B shows the retention of myofiber organization following organoid implantation.

II. Delivery of Bioactive Compounds

Bioactive compounds may be delivered to an organism by growing individual cells in vitro under conditions that result in the formation of an organized tissue producing the bioactive compound and subsequently implanting the organized tissue into the organism (see Section I. for detailed description of organized tissue production). Production of the bioactive compound by the organized tissue is mediated by a foreign DNA sequence present in at least a subset of the cells which make up the implanted tissue.

A variety of bioactive compounds may be delivered by this method, and they may function through intracellular (i.e., within the cells of the organized tissue or organoid), endocrine, autocrine, or paracrine mechanisms. Moreover, the organoid may deliver multiple bioactive compounds either simultaneously or sequentially (e.g., one bioactive compound mediates the delivery of another). Liberation of the bioactive compound from the cells of the organoid may occur by either passive or active processes (e.g., diffusion or secretion).

For example, the bioactive compound may be a hormone, growth factor, or the like which is produced and liberated by the cells of the organoid to act locally or systemically on host tissues. Alternatively, the bioactive compound may function within the cells or on the surface of the cells of the organoid to enhance the uptake or metabolism of compounds from the host tissue or circulation (e.g., lactic acid, low density lipoprotein). Where the organoid serves as a functional and structural adjunct to the host tissue, delivery of growth factors by autocrine or paracrine mechanisms may enhance the integration of the organoid into host tissues. Similarly, where multiple bioactive compounds are produced by the organoid, autocrine delivery of one of the bioactive compounds may be used to regulate the production of one or more of the other bioactive compounds.

The organoid may be implanted by standard laboratory or surgical techniques at a desired anatomical location within the organism. For example, the organoid may be implanted in the same or a different tissue from the tissue of origin of at least one of the individual cells. The location of implantation depends, in part, upon the method of delivery and the identity of the particular bioactive compound to be delivered. For example, an organoid acting as an endocrine organ may be implanted in or adjacent a highly vascularized host tissue. Alternatively, an organoid acting as a paracrine organ is preferably implanted in or adjacent to the host tissue to which the bioactive compound is to be delivered.

The organoid may be implanted by attachment to a host tissue or as a free floating tissue. In addition, attached organoids may be implanted with or without the tissue attachment surfaces used for in vitro tissue formation. Tissues responsive to mechanical forces are preferably implanted by attaching directly to the host tissue or by implanting the organoid coupled to the attachment surfaces so that the organoid is exposed to mechanical forces in vivo. For example, skeletal muscle organoids are preferably implanted by attachment to the host tissue under tension along a longitudinal axis of the organoid. Moreover, the organoids may be permanently or temporarily implanted. Permanent implantation may be preferred, for example, where the organoid produces a bioactive compound which corrects a systemic metabolic error (e.g., delivery of insulin to treat diabetes), whereas temporary implantation may be preferred where only transient delivery of a bioactive compound is desired (e.g., delivery of a growth factor to enhance wound healing). Furthermore, because organoids may be implanted, removed, and maintained in vitro (see FIG. 9A and discussion below), bioactive compounds may be delivered intermittently to the same or a different location in the organism. For example, a skeletal muscle organoid produced from the cells of a human patient (e.g., an autograft) may be implanted at a first anatomical location for a defined period and subsequently implanted at a second location at or after the time of removal.

At least some of the cells of the organoid contain a foreign DNA sequence. The foreign DNA sequence may be extrachromosomal, integrated into the genomic DNA of the organoid cell, or may result from a mutation in the genomic DNA of the organoid cell. In addition, the cells of the organoid may contain multiple foreign DNA sequences. Moreover, the different cells of the organoid may contain different foreign DNA sequences. For example, in one embodiment, a skeletal muscle organoid may include myofibers containing a first foreign DNA sequence and fibroblasts containing a second foreign DNA sequence. Alternatively, the skeletal muscle organoid could include myoblasts from different cell lines, each cell line expressing a foreign DNA sequence encoding a different bioactive compound. These "mosaic" organoids allow the combined and/or synergistic effects of particular bioactive compounds to be exploited. For example, myoblasts expressing growth hormone may be combined with myoblasts expressing an insulin-like growth factor to produce organoids useful in stimulating muscle growth/regeneration. Similarly, myoblasts expressing a bone morphogenetic protein may be combined with myoblasts expressing a parathyroid hormone to produce organoids useful in stimulating bone and cartilage growth/regeneration.

Figure 6:
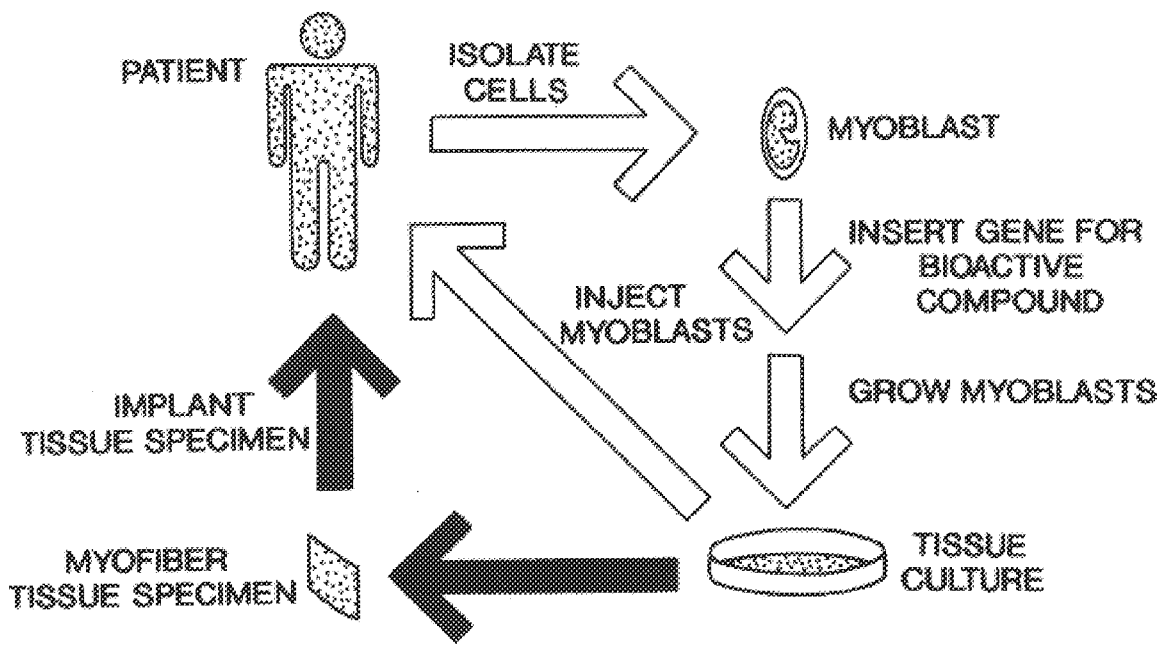
FIG. 6 is a flow chart comparing myoblast and myofiber gene therapy methods.
Figure 7A:
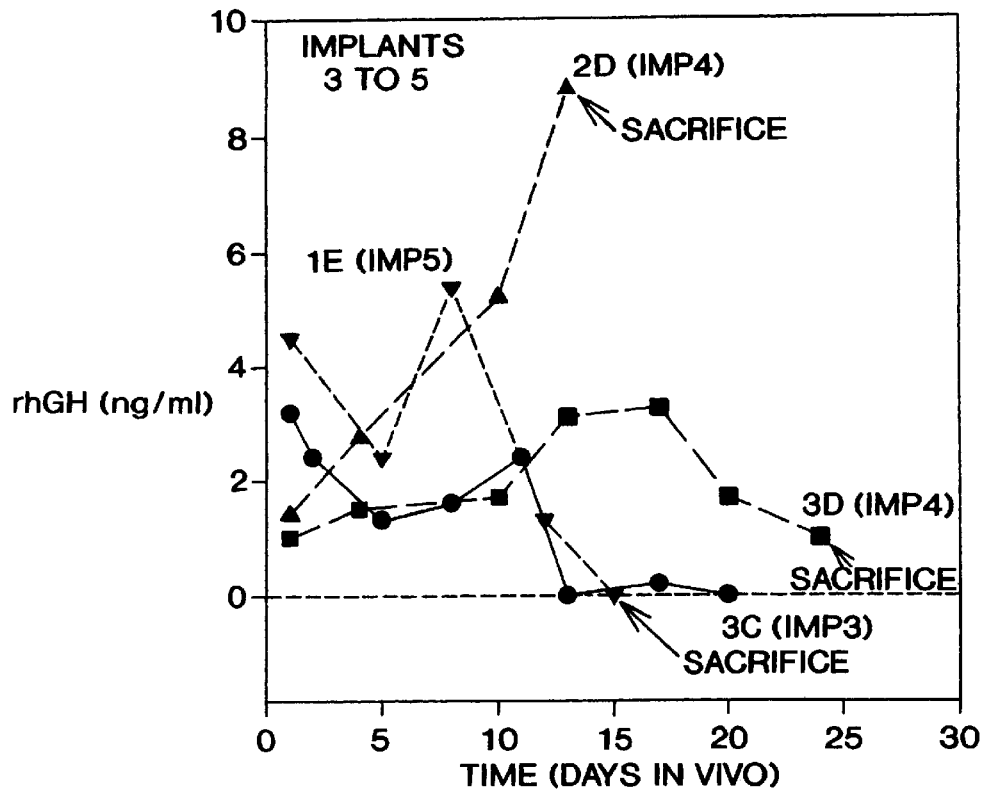
FIGS. 7A–7F are graphs of rhGH serum levels in mice following skeletal muscle organoid implantation.
Figure 7B:
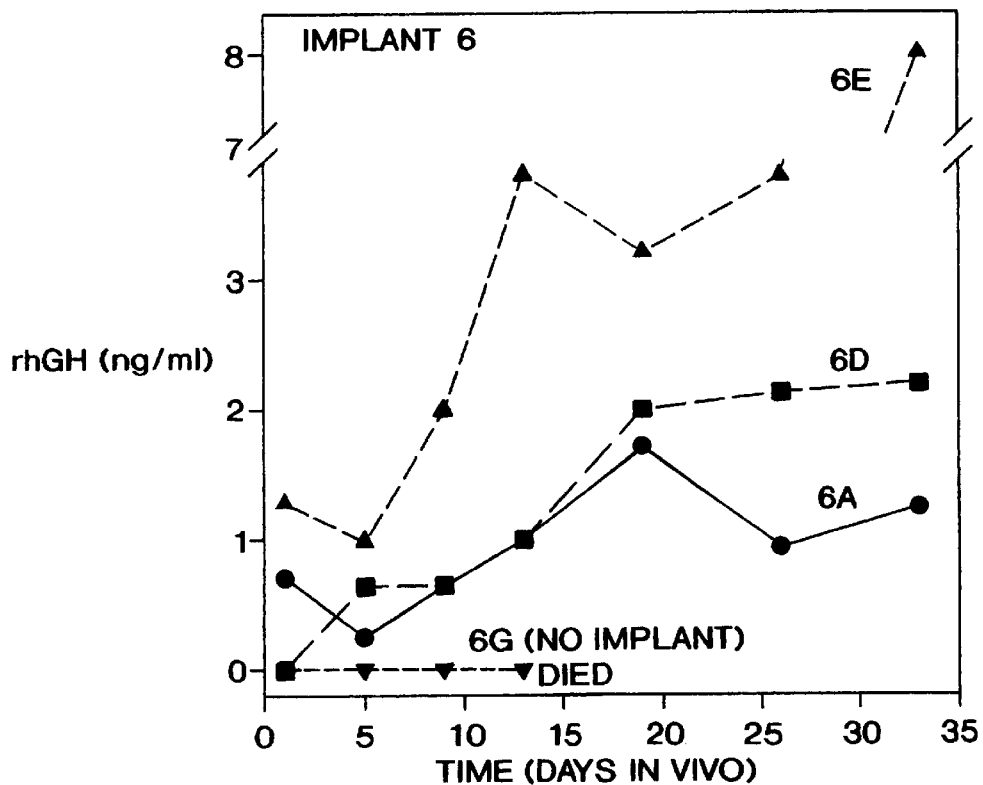
Figure 7C:
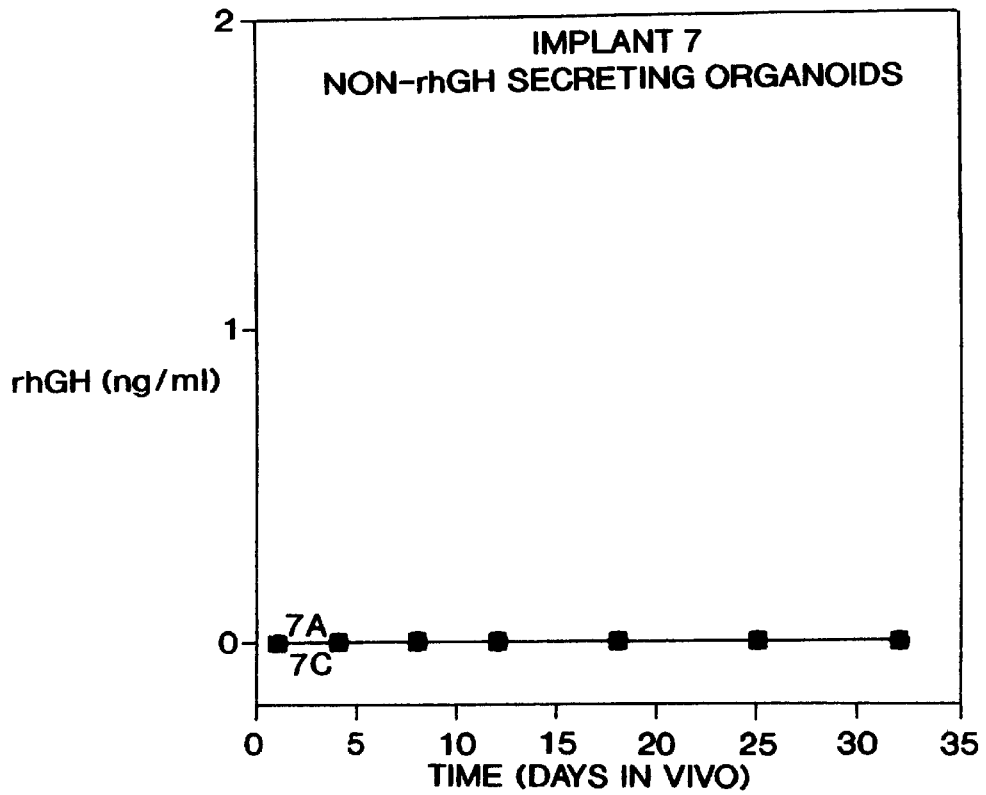
Figure 7D:
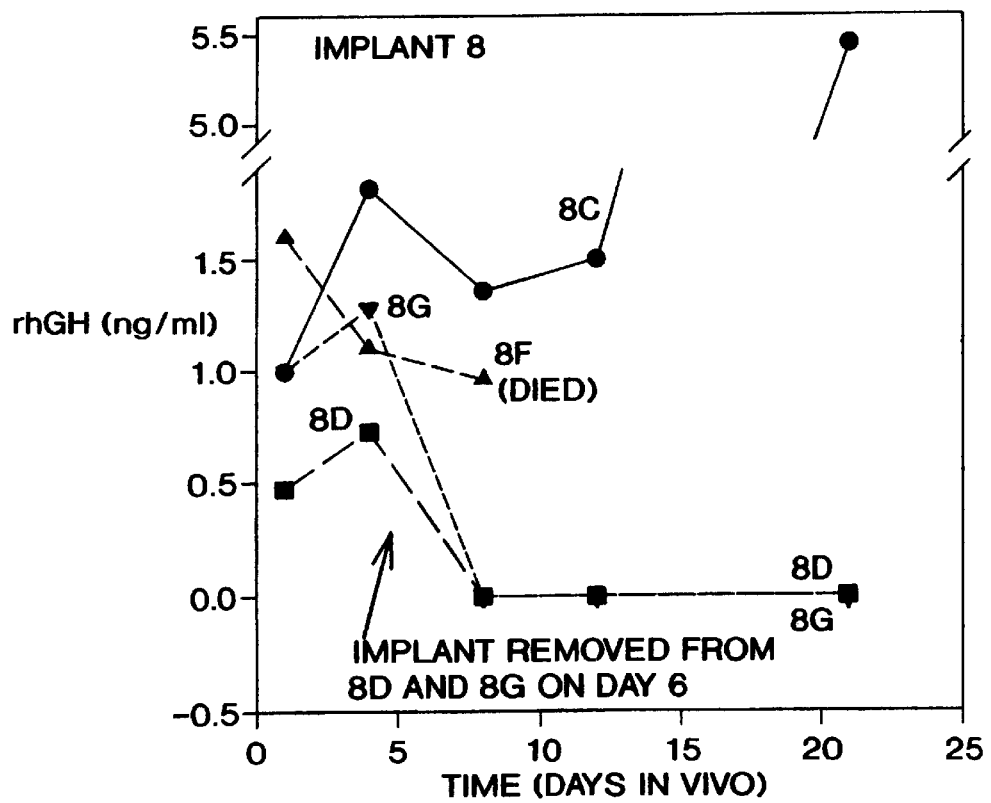
Figure 7E:
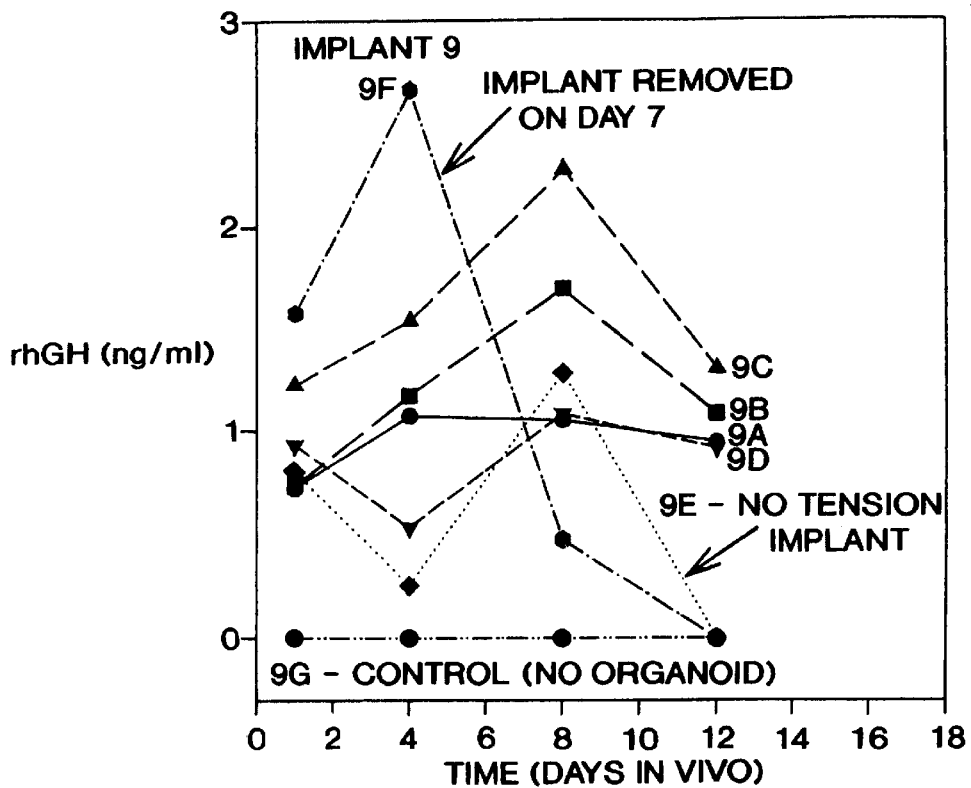
Figure 7F:
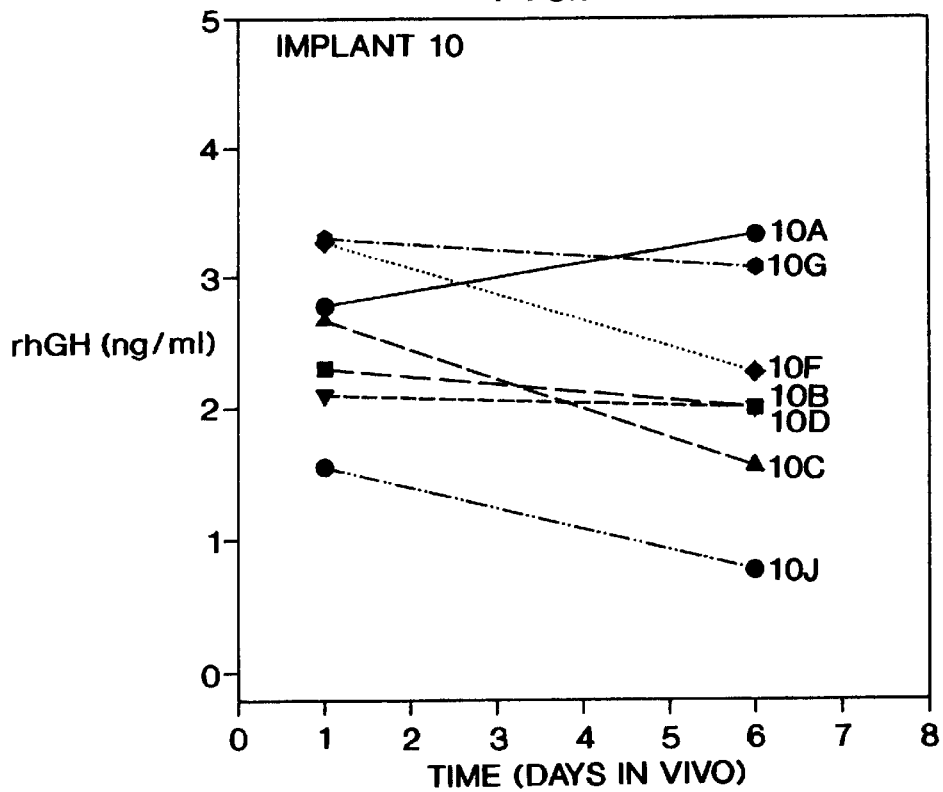

In a preferred embodiment, the foreign DNA sequence encodes a protein which is the bioactive compound. The protein is produced by the cells and liberated from the organoid. Alternatively, the DNA sequence may encode an enzyme which mediates the production of a bioactive compound or a cell surface protein which enhances the uptake and metabolism of compounds from the host tissue or circulation (e.g., lactic acid or low density lipoproteins). The DNA sequence may also encode a DNA binding protein which regulates the transcription of the sequence encoding a bioactive compound or an anti-sense RNA which mediates translation of the mRNA for the bioactive compound. The DNA sequence may also bind trans-acting factors such that the transcription of the sequence (i.e., foreign or native) encoding the bioactive compound is enhanced (e.g., by disinhibition). Furthermore, the foreign DNA sequence may be a cis-acting control element such as a promoter or an enhancer coupled to a native or foreign coding sequence for the bioactive compound or for an enzyme which mediates the production of the bioactive compound. A. Delivery of Human Growth Hormone to Mice by Implanting Skeletal Muscle Organoids FIG. 6 shows an overview and comparison of myoblast and myofiber gene therapy. Both methods generally involve isolating myoblasts from a patient in need of gene therapy, inserting into the myoblasts a DNA sequence encoding a bioactive compound, and expanding the myoblast cell population by in vitro culturing. In contrast to myoblast gene therapy, the myoblasts used in myofiber gene therapy are further cultured in vitro under conditions which result in the formation of an organoid having in vivo-like gross and cellular morphology. The organoid is subsequently implanted into the patient to deliver the bioactive compound.

To carry out the delivery of a bioactive compound to an organism, skeletal muscle organoids were formed in vitro, as described above, from C2C12 mouse skeletal muscle myoblasts stably co-transfected with recombinant human growth hormone-expressing and β-galactosidase-expressing constructs. Prior to implantation, in vitro production of recombinant human growth hormone ("rhGH") was measured by radioimmunoassay according to the manufacturer's instructions (Nichols Institute Diagnostics, San Juan Capistrano, Calif.). Between three and twenty-four days of culture, the mean rhGH production ranged between 1.0 and 3.5 $\mu$g/day/organoid (see Table 1).

TABLE 1

IN VITRO PREIMPLANT SUMMARY

| Experiment | Date | Initial Cell # per Organoid ($\times 10^6$) | Age of Organoid (Days) | Mean rhGH ($\mu$g/day/organoid) (N =) | Treatment of Organoids |
|---|---|---|---|---|---|
| IMPLANT 1 | 8/24 | 6 | 3 | 1.9 (2) | none |
|  |  |  | 7 | 3.5 (2) |  |
| IMPLANT 2 | 9/21 | — | — | — | — |
| IMPLANT 3 | 10/5 | 4 | 7 | 1.7–2.8 (7) | none |
|  |  |  | 12 | 1.9–2.5 (6) |  |
| IMPLANT 4 | 10/20 | 2 | 21 | 2.2–2.6 (5) | none |
| IMPLANT 5 | 10/25 | 2 | 12 | 2.9 (12) | no cytosine arabinoside ("araC") |
|  |  |  | 12 | 2.0 (4) | 1 ug/ml araC for 4 days |
| IMPLANT 6 | 11/8 | 3 | 19 | 1.0 (6) | no araC |
|  |  |  |  | 1.0 (6) | 1 ug/ml araC for 5 days |
| IMPLANT 7 | 11/9 | 3 (non-rhGH secreting) | 17 | 0 (3) | control experiment |
| IMPLANT 8 | 11/3 | 2 | 14–20 | 1.5 to 2.2 (6) | no araC |
|  |  |  |  | 1.2 to 1.6 (6) | 1 ug/ml araC for 5 days |
| IMPLANT 9 | 11/30 | 1–2 | 24 | 1.7 to 2.4 (8) | 1 ug/ml araC for 8 days |
| IMPLANT 10 | 12/5 | 1.5–2.0 | 20 | 2.1 to 2.9 (14) | 1 ug/ml araC for 4 days |

The organoids were implanted into adult C3HeB/FeJ mice (i.e., syngeneic to C2C12 cells) by the following method. Mice were weighed to determine dosages of cyclosporine and anesthetic. One hour prior to the surgical implantation of the organoid, each mouse was given an injection of 60 mg/kg of cyclosporine A. Each mouse was then selected in turn and anesthetized by intramuscular injection of 55 mg/kg Ketamine, 1 mg/kg Promazine, and 5 mg/kg Xylazine. The site of implantation was then depilatated with Nair™ or by shaving, and prepped for aseptic surgery. For organoids implanted subcutaneously, a four to six centimeter long incision was made along the back, the organoid was implanted in either a free floating state or fixed under tension (e.g., attached to the tissue attachment surfaces), and the incision was closed with four to six sutures of 4.0-black silk.

For organoids implanted intramuscularly, a 15 to 30 millimeter incision was made parallel to the anterior tibialis muscle (e.g., anteriolateral aspect of the lower hind limb) to provide access to the muscle sheath. The anterior tibialis was gently split with forceps from tendon to tendon parallel to the muscle belly, thus providing a cavity for insertion of the organoid. The organoid was carefully removed from the vessel by prying the ends off the tissue attachment surfaces with sterile forceps and inserting it, under resting tension, in the implantation site. The incision was closed as described above. Mice were then followed post-surgically for distress and upon regaining consciousness were returned to an animal care facility. Cyclosporine injections are repeated daily for the duration of the experiment. The experimental protocol for the implantation of skeletal muscle organoids is summarized in Table 2 below.

TABLE 2

IN VIVO PROTOCOL SUMMARY

| Experiment | Date | Site of Implant | # of Surviving Animals | rhGH Producers (# and method) of implant |
|---|---|---|---|---|
| IMPLANT 1 | 8/24 | intramuscular free-floating | 2 of 2 | 0 (1 free) |
| IMPLANT 2 | 9/21 | controls only - cyclosporine dose-response | 6 of 6 | no organoids implanted |
| IMPLANT 3 | 10/5 | subcutaneous free-floating | 3 of 4 | 1 (3C-2 free) |
| IMPLANT 4 | 10/20 | subcutaneous fixed under tension | 2 of 3 | 2 (2D-2 fixed) (3D-1 fixed/ 1 free) |
| IMPLANT 5 | 10/25 | subcutaneous fixed under tension | 1 of 2 | 1 (1E-3 fixed) |
| IMPLANT 6 | 11/8 | subcutaneous fixed under tension | 4 of 7 | 3 (6A, 6D, 6E-1 fixed) (6G-no organoid) |
| IMPLANT 7 | 11/9 | subcutaneous fixed under tension | 2 of 3 | 0 (7A and 7C-1 fixed, non-rhGH secreting organoid) |
| IMPLANT 8 | 11/13 | subcutaneous fixed under tension | 5 of 8 | 4 (8C, 8D, 8F and 8G-1 fixed) |
| IMPLANT 9 | 11/30 | subcutaneous fixed under tension or free-floating | 7 of 7 | 5 (9A, 9B, 9C, 9D and 9F-1 fixed) 1 (9E-1 free) (9G-no organoid) |
| IMPLANT 10 | 12/5 | subcutaneous fixed under tension | 7 of 11 | 7 (10A, 10B, 10C, 10D, 10F, 10G, and 10J-1 fixed) |

Blood was collected every one to seven days by tail bleeding from the mice. Sera concentrations of rhGH were measured by radioimmunoassay according to the manufacturer's instructions (Nichols Institute Diagnostics, San Juan Capistrano, Calif.).

Figure 8A:
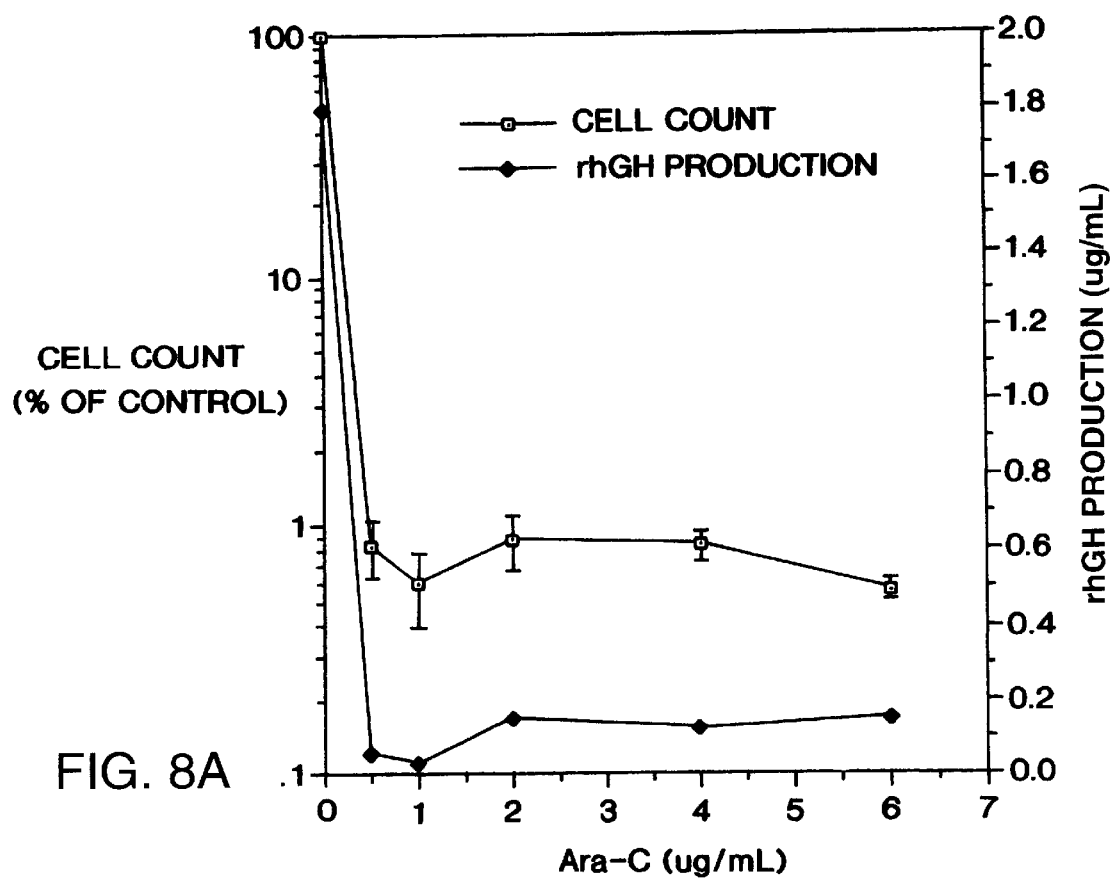
FIGS. 8A–8B are graphs of the effects of cytosine arabinoside on rhGH-secreting C2C12 proliferating myoblasts and post-mitotic myofibers.
Figure 8B:
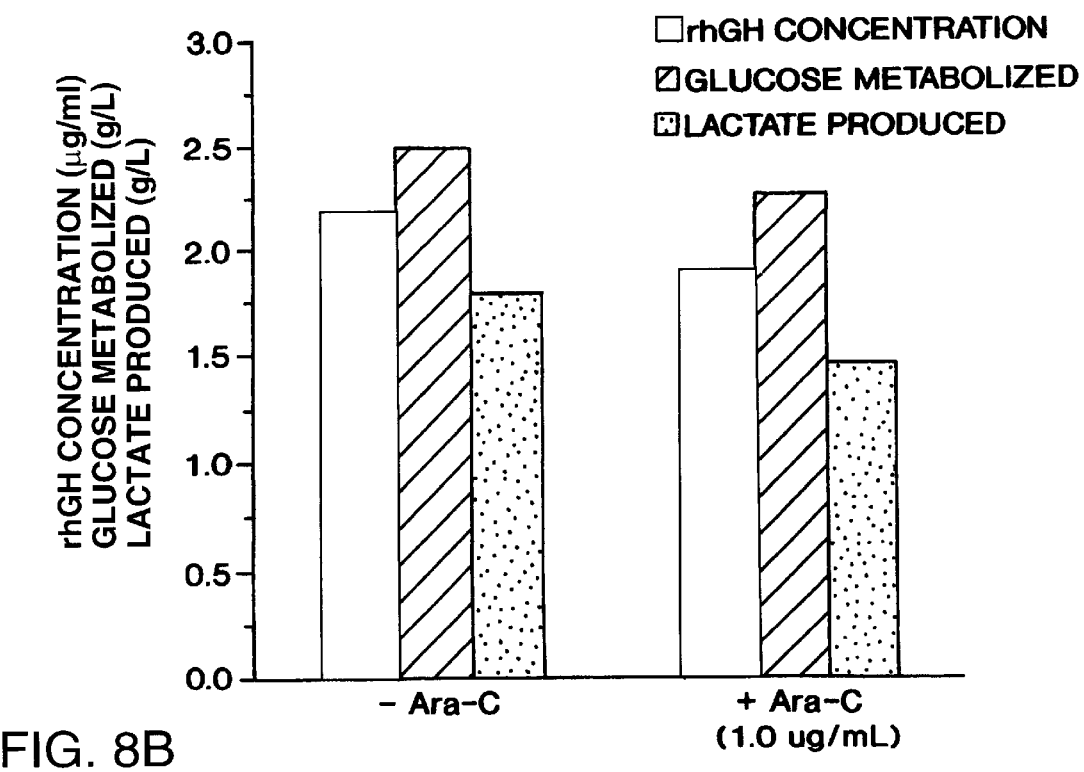
Figure 9C:
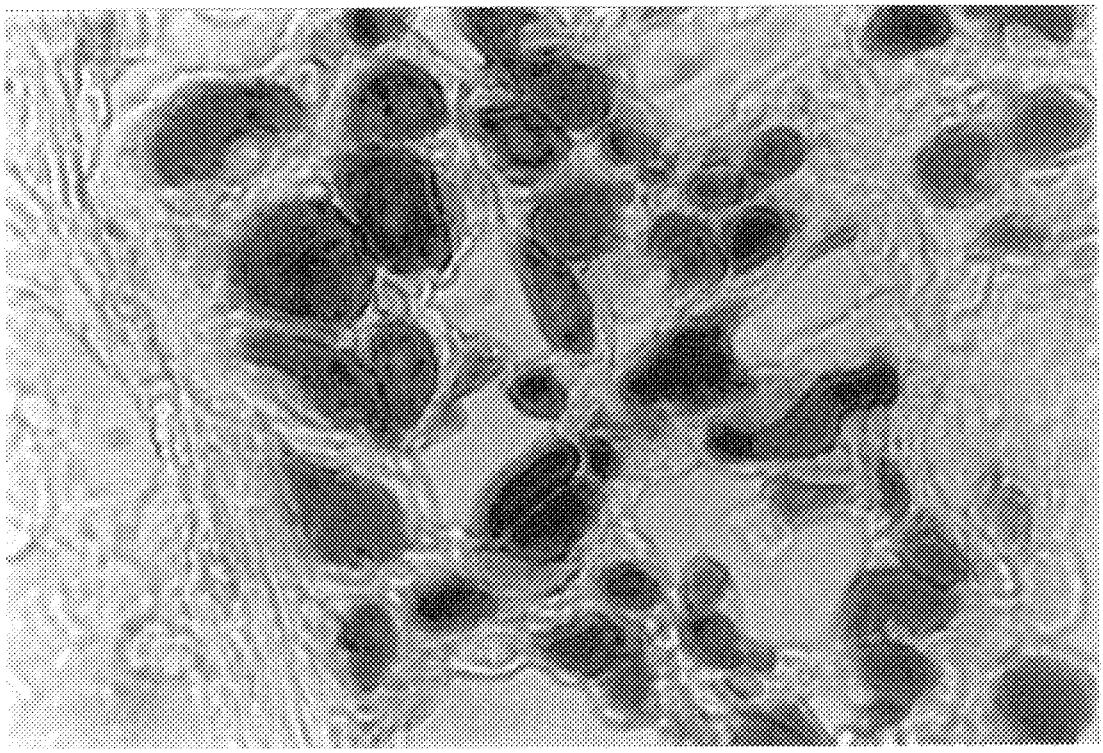

As shown in FIGS. 7A–7F, rhGH was detected in the blood of animals receiving rhGH organoid implants, but not in controls (6G, 7A, 7C, and 9G) for up to thirty-three days post-implantation. Serum concentrations were elevated as high as approximately 5.5 to 9 ng/ml in animals receiving multiple implants of rhGH producing organoids (1E, 2D), whereas serum from animals receiving no implant (6G, 9G) or implants of non-rhGH secreting organoids (7A and 7C) contained no detectable rhGH. In addition, animals receiving organoids treated in vitro with cytosine arabinoside prior to implantation (1E, 6E, 8D, 8F, 8G, 9A through 9F, and 10A through 10J) demonstrated serum rhGH levels comparable to those of animals receiving implants which were not treated in vitro with cytosine arabinoside prior to implantation (i.e., 2D, 3C, 3D, 6A, 6D, and 8C). Under the conditions used in this study, cytosine arabinoside treatment kills greater than 99% of proliferating C2C12 myoblasts while having only a minor effect on myofiber metabolism and rhGH secretion (FIG. 8). Moreover, FIG. 9C shows that the rhGH gene and the β-galactosidase gene are only expressed in post-mitotic myofibers. These results demonstrate that organoids including substantially post-mitotic cells can deliver therapeutic levels of a bioactive compound for up to thirty-three days post-implantation.

It is noteworthy that within forty-eight hours following the removal of implants (i.e., 8D, 8G and 9F), rhGH was undetectable in the sera of animals previously having serum concentrations as high as 2.6 ng/ml. These data demonstrate the reversibility of delivering bioactive compounds by this method. In addition, organoids removed from animals may be re-incubated in vitro (see e.g., FIG. 9A). For example, the two organoids implanted into animal 3D produced 188 ng/day of rhGH in vitro post-implantation. These data suggest the feasibility of removing organoids and subsequently reimplanting them such that bioactive compounds may be delivered during multiple treatment periods separated in time. Moreover, the data suggest the feasibility of transplanting sequentially, at different sites within the same organism, organoids functioning as paracrine organs.

The rhGH production of 188 ng/day in vitro by organoids from animal 3D and the in vivo serum levels of 1.0 ng/ml on day twenty-four (i.e., just prior to removal) suggest a 188-fold difference between organoid production and steady state circulating levels of rhGH in the animal. These results compare favorably to the 500-fold difference between rhGH concentrations delivered by direct subcutaneous injection and steady state circulating levels, (Yang et al. *Circulation* 92:262–267, 1995 (1000 $\mu$g/day rhGH by direct subcutaneous injection produced 2 $\mu$g/ml serum concentrations in rats). It is also noteworthy that the organoid maintained in vivo under tension produced approximately 144 ng/ml when placed in vitro on removal from the animal, while the free floating organoid produced only 40 ng/ml when placed in vitro on removal from the animal. In addition, an organoid implanted under no tension (9E) was a poorer producer of rhGH in vivo than those placed under tension (9A, 9B, 9C). These results suggest that maintaining organoids under tension enhances the production and delivery of bioactive compounds.

B. Delivery of Bone Morphogenetic Protein to an Organism by Implanting Skeletal Muscle Organoids 1. Transduction and Selection of C2C12 Myoblasts Expressing rhBMP-6

φ2 packaging cells producing high titers (>1×10$^7$ pfu) of retrovirus containing the pLX(rhBMP-6)SN expression vector were provided by Dr. Vladimir Drozdoff, Department of Medicine, Vanderbilt University. Myoblast cell cultures, 50% confluent in T-75 flasks, were incubated for eight hours in 20 ml of conditioned media from the high viral titer packaging cells. The media was supplemented with 4 $\mu$g/ml of polybreen. After eight hours, the cells were placed in DMEM +10% fetal calf serum containing 2 $\mu$g/ml of polybreen, and cultured for an additional 48–72 hr, or until the cells had undergone one or two additional divisions. The transduced cells were then harvested, counted, and plated out as single cell clones in four 12-well plates. The single cell clones were selected by culturing in DMEM +10% fetal calf serum containing 400 $\mu$g/ml of G418. Single cell colonies began to appear after 2–3 weeks in culture. These colonies were first expanded to a single T-25 flask, and then expanded to two T-150 flasks which were grown to 90% confluency. The first flask was harvested for storage of cells in liquid nitrogen, and the second flask was processed for total RNA.

Alternatively, myoblasts are transducible by direct incubation with plasmids containing bone morphogenetic protein genes (e.g., mouse BMP-4, Fang, J., et al., *Stimulation of new bone formation by direct transfer of osteogenic plasmid genes,* Proc. Natl. Acad. Sci. U.S.A. 93:5753–5758, 1996; human BMP-1, BMP-2A and BMP-3, Wozney, J. M., et al., *Novel regulators of bone formation: molecular clones and activities,* Science 242:1528–1532, 1988; human BMP-4, Ahrens, M., et al., *Expression of human bone morphogenetic proteins-2 or -4 in murine mesenchymal progenitor C3H10T1/2 cells induces differentiation into distinct mesenchymal cell lineages,* DNA and Cell Biology 32:871–880, 1993). For example, myoblasts may be successfully transduced by standard calcium phosphate coprecipitation or lipofection.

Figure 10A:
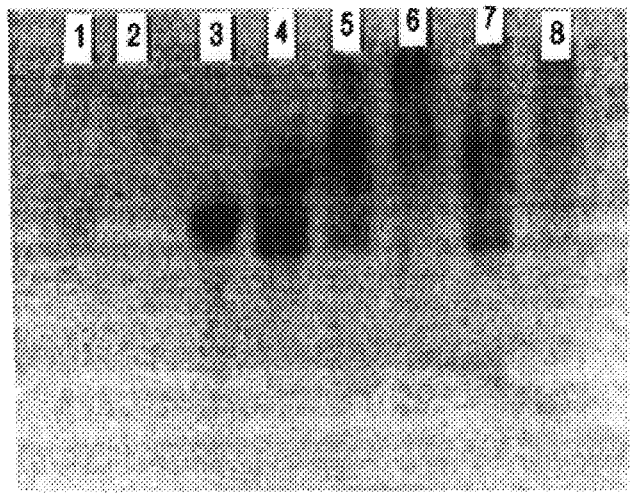
FIGS. 10A–10C are Northern blots of rhBMP-6 mRNA levels in C2C12 cells retrovirally-transduced with a rhBMP-6 gene.
Figure 10B:
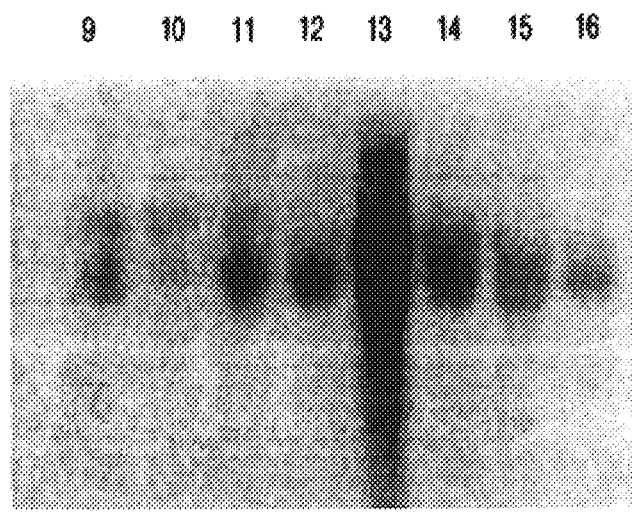
Figure 10C:
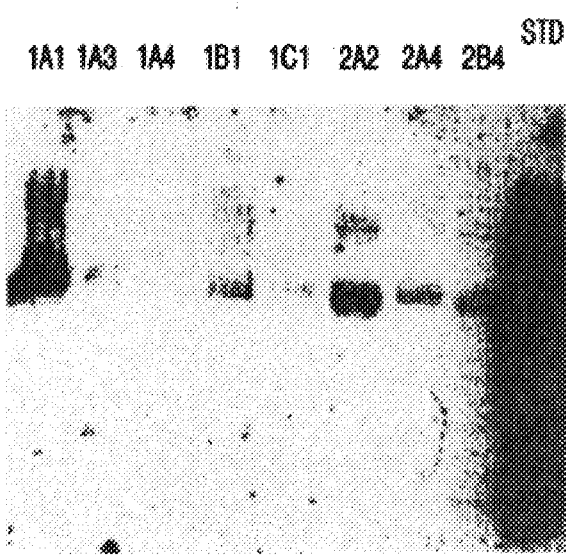
Figure 11:
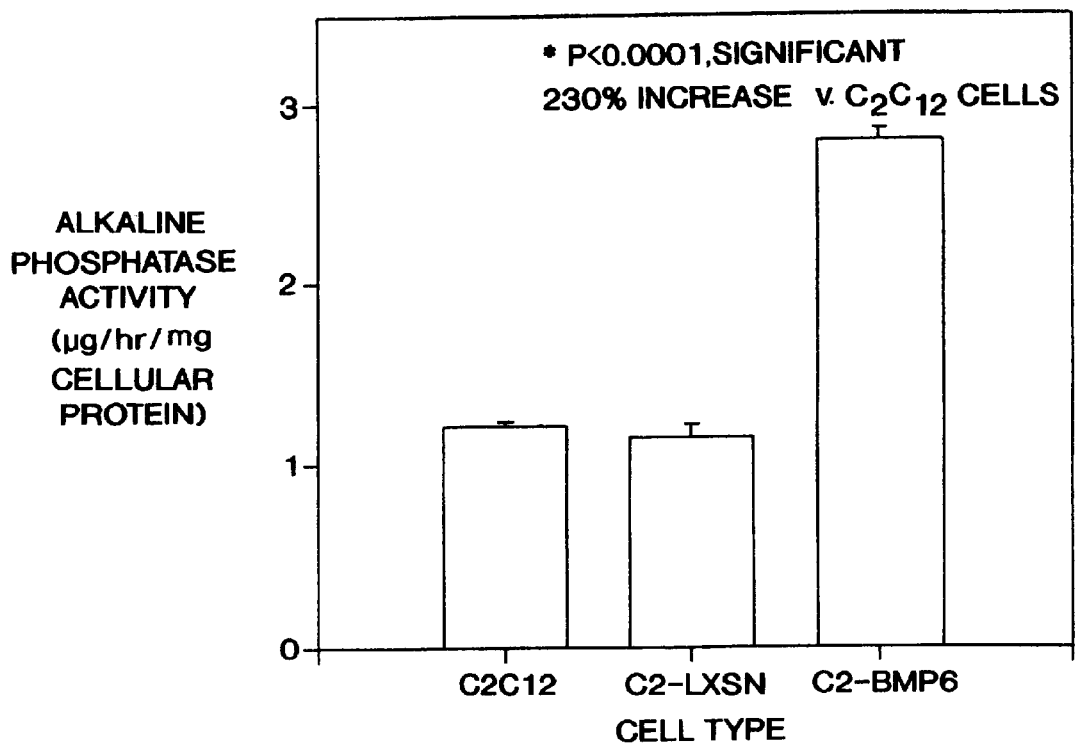
FIG. 11 is a graph of alkaline phosphatase activity in controls and C2C12 cells retrovirally-transduced with a rhBMP-6 gene.

Northern blot analysis was performed on the cell clones with 20 $\mu$g of total or standard RNA per lane (FIGS. 10A–10C). The blots were hybridized with a cDNA probe to rhBMP-6 (supplied by Genetics Institute, Cambridge, Mass.). Referring to FIGS. 10A and 10B, clones expressing high levels of rhBMP-6 mRNA (e.g., cell line 4A1 in lane 13 of FIG. 10B) were expanded and recloned from single cell colonies. Referring to FIG. 10C, subclones of cell line 4A1 were rescreened by Northern blot analysis, and clones 1A1 and 2A2 expressed high levels of rhBMP-6 MRNA relative to the other clones. Cell colonies retaining high expression of rhBMP-6 were harvested and banked in liquid nitrogen.

2. Expression of Biologically Active BMP-6

The biological activity of rhBMP-6 in cell colonies retaining high expression of rhBMP-6 (i.e., $C_2$-BMP6 cells) was determined by measuring alkaline phosphate activity (i.e., an osteoblastic marker) in the cells after 14 days in culture. Normal C2C12 cells (i.e., non-transduced cells) and C2C12 cells transduced with the LXSN vector alone (i.e., $C_2$-LXSN cells) were used as controls.

Cells were harvested after 14 days as follows. Wells containing the cells were rinsed with phosphate buffered saline (0.1 m, pH 7.4; PBS) and then typsinized with five drops per well of 0.05% trypsin/EDTA solution in PBS. The trypsin/EDTA was neutralized with 500 $\mu$l serum-containing media per well, and cells were transferred to microcentrifuge tubes and centrifuged at 900 rpm for four minutes to pellet the cells. Cell pellets were resuspended and lysed in 500 Al of TXM buffer (10 mM Tris HCL; 1.0 mM magnesium chloride; 0.02 mM zinc chloride; 0.1% Triton X100; and 0.02% sodium azide), and stored at −20° C. until assayed or assayed immediately for alkaline phosphate activity as follows.

One hundred microliters of cell lysate, blank (buffer minus substrate), or standard (5 mM p-nitrophenol in buffer) was added to a tube containing 400 μl of alkaline phosphate assay substrate and buffer (0.1 mg glycine; 2.0 mM magnesium chloride; 2 mg/ml p-nitrophenyl phosphate) and incubated at 37° C. for 30 min. The reaction was stopped by adding 500 μl of 0.25N NaOH, and the optical density at 410 nm was read on a spectrophotometer. The total cellular protein in each sample was measured with a Bio-Rad™ protein assay essentially according to the manufacturer's instructions (Bio-Rad Laboratories, Hercules, Calif.) and alkaline phosphatase activities calculated as follows:

$$\text{Total Alkaline Phosphatase Activity for Sample} \left[\frac{\mu g}{\text{hour}}\right] = \frac{(2 \times \text{Sample Optical Density} \times \text{Dilution Factor})}{(\text{Average of Standard Optical Densities})}$$

$$\text{Alkaline Phosphatase Activity} \left[\frac{\mu g/\text{hour}}{\text{mg cellular protein}}\right] = \frac{\text{Total Alkaline Phosphatase Activity for Sample}}{\text{Total Cellular Protein for Sample}}$$

3. Delivery of BMP-6 by Implanting Skeletal Muscle Organoids

The ability of $C_2$-BMP6 cells to differentiate and fuse to form skeletal muscle myofibers was analyzed by morphometric analysis and expression of the muscle-specific protein sarcomeric tropomyosin after six to fourteen days in culture. Normal C2C12 cells and $C_2$-LXSN cells were used as controls.

Normal C2C12 cells, C2-LXSN cells, and $C_2$-BMP6 cells were cultured separately in T-75 flasks. At 80% confluence, all cell types were individually subcultured and plated into four well-plates (i.e., 15-mm diameter wells pretreated with a collagen spray 1 mg/ml of rat-tail collagen, type I in 1% acetic acid). The cells were plated at a density of 100,000 cells per well in 750 μl of growth medium (DMEM-high glucose; 10% calf serum; 10% fetal calf serum; 100 units/ml penicillin; and 0.1 mg/ml streptomycin) and incubated in a humidified, 37° C., 5% $CO_2$ atmosphere.

The cells were fed 750 μl warm growth medium per well every 48 hours (i.e., day 2 and day 4 post-plating). Five days post-plating when all groups showed ~100% confluence, the cells were switched to a low serum fusion medium to promote fusion (DMEM-high glucose; 2% horse serum; 100 units/ml penicillin; 0.1 mg/ml streptomycin). The cells were fed fusion medium on days six, eight and ten post-plating. On day 12 post-plating, the cells were switched to a maintenance medium (DMEM-high glucose; 10% horse serum; 5% fetal calf serum; 100 units/ml penicillin; and 0.1 mg/ml streptomycin). The experiment was terminated on day 14.

Plates were fixed for morphometric analysis 6, 8, 12 and 14 days post-plating as follows. Cells were quickly rinsed twice with Eagle's balanced salt solution (EBSS), fixed with Histochoice™ for thirty minutes at room temperature, and incubated twice for ten-minutes in EBSS. The samples were then stored in fresh EBSS at 4° C. until used for immuno-histochemical analysis.

From storage, samples were warmed to room temperature and rinsed with phosphate buffer saline (PBS; 10 mM, pH 7.4). Samples were then incubated with the primary antibody, anti-sarcomeric tropomyosin (1:100 dilution) in 0.5% Tween 20/PBS for thirty minutes at room temperature, followed by PBS rinsing. Secondary antibody and avidin biotinylated enzyme steps were performed essentially according to the Vectastains Elite ABC Kit protocol. Samples were then developed with diaminobenzidine tetrahydrochloride (DAB) reagent to produce a brown precipitate, and then lightly counterstained with hematoxylin.

Figure 12A:
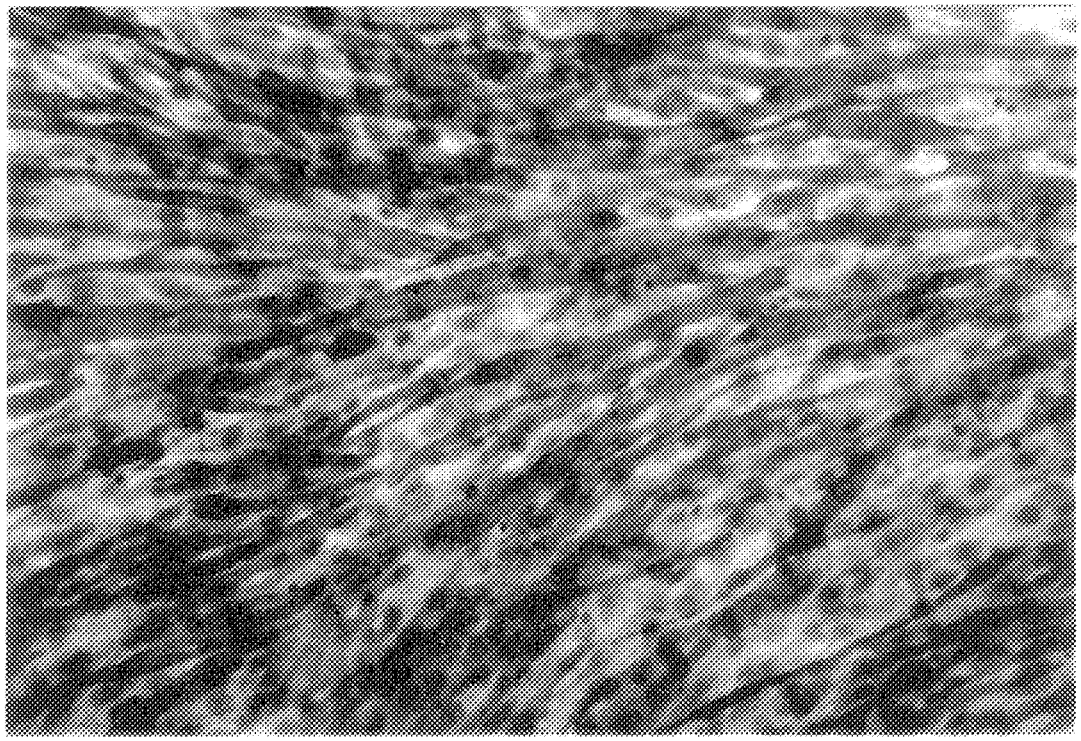
FIGS. 12A and 12B are micrographs of C2C12 cells retrovirally-transduced with a rhBMP-6 gene which have been stained for sarcomeric tropomyosin.
Figure 12B:

Referring to FIGS. 12A (Day 8 post-plating) and 12B (Day 14 post-plating), the ability of $C_2$-BMP6 cells to differentiate and fuse to form skeletal muscle myofibers is demonstrated by morphometric analysis (i.e., the presence of longitudinally-oriented multinucleated fibers) and by the presence of sarcomeric tropomyosin (i.e., a muscle-specific protein expressed in differentiated skeletal muscle myofibers but not in undifferentiated, proliferative myoblasts). Because the expression of a biologically active bone morphogenetic protein does not impair the ability of skeletal muscle myoblasts to differentiate and fuse to form skeletal muscle myofibers, skeletal muscle organoids which express bone morphogenetic proteins are produced as described above (see Section I), and are used to deliver bone morphogenetic proteins to an organism also as described above (see Section II).

Because bone morphogenetic proteins are extracellular molecules, skeletal muscle organoid delivery of the protein may be through endocrine, autocrine, or paracrine mechanisms. In a preferred embodiment, the organoid may function as a paracrine organ to deliver a bone morphogenetic protein to chondroblastic or osteoblastic precursor cells. For example, a skeletal muscle organoid expressing a bone morphogenetic protein may be implanted adjacent a non-union fracture to stimulate endochondral bone formation and repair. Alternatively, a skeletal muscle organoid could be implanted in an organism adjacent skeletal tissues which are susceptible to degeneration and fracture consequent to aging (e.g., the hip joint or spinal column of elderly humans). Similarly, bone morphogenetic protein expressing organoids may be employed to treat systemic or regional osteoporosis (e.g., of the spine, femoral neck, and scapular regions of elderly humans). Skeletal muscle organoids expressing bone morphogenetic proteins may also function to accelerate cartilage repair and the healing of segmental defects or bony fusions.

What is claimed is:

1. A method of delivering a protein to a mammal comprising the steps of:

growing in vitro a plurality of cells from the same species as said mammal, wherein at least a subset of said cells comprise a foreign DNA sequence operably linked to a promoter and encoding a protein, and wherein said cells are mixed with an extracellular matrix to create a suspension;

placing said suspension in a vessel having a three-dimensional geometry approximating the in vivo gross morphology of a tissue of interest, said vessel having attachment surfaces thereon; and allowing the suspension to coalesce;

culturing said coalesced suspension under conditions in which said cells connect to said attachment surfaces and form an organized tissue having an in vivo-like gross and cellular morphology of said tissue of interest, and wherein the organized tissue further is comprised of post-mitotic cells; and implanting said tissue into said mammal, whereby said protein is produced and delivered to said mammal, whereby said protein is of a type or produced in an amount not produced by said tissue of interest lacking said foreign DNA sequence, wherein said protein is produced sufficiently to provide a therapeutic effect to the mammal upon implantation of said organized tissue into said mammal.

2. The method of claim 1, further comprising the steps of: removing said tissue from said mammal to terminate delivery of said protein.

3. The method of claim 2, further comprising, following said removal step, the step of:
culturing said tissue in vitro under conditions which preserve its in vivo viability.

4. The method of claim 3, further comprising, following said culturing step, the step of:
reimplanting said tissue into said mammal to deliver said protein to said mammal.

5. The method of claim 1, wherein said tissue is implanted into the tissue of origin of at least one of said cells.

6. The method of claim 1, wherein said DNA sequence mediates the production of two proteins.

7. The method of claim 1, wherein said protein is a growth factor.

8. The method of claim 1, wherein, during said growing step, a force is exerted parallel to a dimension of said tissue.

9. The method of claim 8, wherein said force is exerted on said individual cells during growth in vitro and on said organized tissue during implantation in vivo.

10. The method of claim 1, wherein said tissue comprises skeletal muscle.

11. The method of claim 1, wherein said tissue comprises myotubes.

12. The method of claim 1, wherein said cells comprise myotubes.

13. The method of claim 1, wherein said mammal is a human.

14. A method of delivering a protein to a mammal comprising the steps of:
growing in vitro a plurality of mammalian cells from the same species as said mammal, wherein at least a subset of said cells comprise a foreign DNA sequence operably linked to a promoter and encoding a protein, and wherein said cells are mixed with an extracellular matrix to create a suspension;
placing said suspension in a vessel wherein the cells form an organized tissue of interest having a three dimensional cellular organization which is retained upon implantation into a mammal, and wherein the organized tissue is further comprised of post-mitotic cells; and
implanting said organized tissue into said mammal, whereby said protein is produced and delivered to said mammal sufficiently to provide a therapeutic effect to the mammal, whereby said protein is of a type or produced in an amount not produced by a tissue lacking said foreign DNA sequence.

15. A method of providing a protein to a mammal in therapeutic need thereof:
implanting into said mammal an organized tissue having a three-dimensional geometry approximating the in vivo gross morphology of a tissue of interest, wherein the organized tissue is comprised of post-mitotic cells from the same species as said mammal and wherein at least a subset of cells of said organized tissue comprises a foreign DNA sequence operatively linked to a promoter and encoding a protein, and wherein said protein is produced sufficiently to provide a therapeutic effect to the mammal upon implantation of said organized tissue into said mammal.

16. A method of providing a protein to a mammal in therapeutic need thereof:
implanting into said mammal an organized tissue comprising post-mitotic cells from the same species as said mammal and having a three-dimensional geometry approximating the in vivo gross morphology of a tissue of interest that is retained upon implantation of said organized tissue into a mammal, wherein at least a subset of the cells of said organized tissue comprise a foreign DNA sequence operatively linked to a promoter and encoding a protein, and wherein said protein is produced sufficiently to provide a therapeutic effect to the mammal upon implantation of said organized tissue into said mammal.

17. The method of claim 15 or 16, said protein being growth hormone.

18. An in vitro method for producing an organized tissue which has an in vivo-like gross and cellular morphology comprising the steps of:
providing cells of said tissue, wherein at least a subset of said cells comprise a foreign DNA sequence operably linked to a promoter and encoding a protein, wherein said cells are mixed with an extracellular matrix to create a suspension;
placing said suspension in a vessel having a three-dimensional geometry approximating the in vivo gross morphology of a tissue of interest, said vessel having attachment surfaces thereon; and
allowing the suspension to coalesce; and
culturing said coalesced suspension under conditions in which said cells connect to said attachment surfaces and form an organized tissue having an in vivo-like gross and cellular morphology of said tissue of interest, wherein the organized tissue is further comprised of post-mitotic cells and wherein at least a subset of the cells said organized tissue comprise said DNA sequence.

19. The method of claim 18, wherein the step of providing comprises isolating primary cells of at least one of the cell types comprising said tissue of interest.

20. The method of claim 18, wherein the step of providing comprises utilizing immortalized cells of at least one of the cell types comprising said tissue.

21. The method of claim 18, wherein prior to the step of providing, a foreign DNA sequence operably linked to a promoter and encoding a protein is introduced to at least a subset of said cells.

22. The method of claim 18, wherein said cells comprise skeletal muscle cells.

23. The method of claim 18, wherein said coalesced suspension exerts a force on said cells parallel to a dimension of said vessel.

24. The method of claim 18, wherein said cells are aligned parallel to a dimension of said vessel.

25. The method of claim 24, wherein said vessel is substantially semi-cylindrical in shape.

26. The method of claim 25, wherein said attachment surfaces are positioned at opposite ends of said vessel.

27. The method of claim 18, wherein said organized tissue produces said protein.

28. An organized tissue comprising post-mitotic cells, said organized tissue having an in vivo gross cellular morphology and producing a protein of a type or produced in an amount not produced normally by a tissue of interest, produced according to the method of claim 17.

29. An organized tissue producing a protein of a type or produced in an amount not produced normally by a tissue of interest, where the organized tissue is produced by the steps of:

mixing a plurality of cells with an extracellular matrix to create a suspension, wherein at least a subset of said cells comprise a foreign DNA sequence operably linked to a promoter and encoding a protein;

placing said suspension in a vessel having a three-dimensional geometry approximating the in vivo gross morphology of said tissue of interest, said vessel having attachment surfaces thereon; and allowing the suspension to coalesce; and culturing said coalesced suspension under conditions in which said cells connect to said attachment surfaces and form an organized tissue having an in vivo-like gross and cellular morphology of said tissue of interest, and wherein the organized tissue is further comprised of post-mitotic cells, and;

wherein the protein is produced at detectable levels in said tissue.

30. An organized tissue, wherein the organized tissue has an in vivo-like gross and cellular morphology of a tissue of interest and produces a protein of a type or produced in an amount not produced normally by said tissue of interest comprising:

a plurality of cells, wherein at least a subset of said cells comprise a foreign DNA sequence operably linked to a promoter and encoding a protein, wherein said cells form an organized tissue approximating the in vivo gross morphology of said tissue of interest and wherein the organized tissue is further comprised of post-mitotic cells, and;

wherein the protein is produced at detectable levels in said tissue.

31. The organized tissue of claim 30, wherein said tissue is skeletal muscle.

32. An organized tissue producing a protein produced by the steps of:

mixing a plurality of mammalian cells, wherein at least a subset of said cells comprise a foreign DNA sequence operably linked to a promoter and encoding a protein, wherein said cells are mixed with an extracellular matrix to create a suspension;

placing said suspension in a vessel having a three-dimensional geometry approximating the in vivo gross morphology of a tissue of interest, said vessel having attachment surfaces thereon; and allowing the suspension to coalesce; and culturing said coalesced suspension under conditions in which said cells connect to said attachment surfaces, wherein said suspension of cells forms an organized tissue that has a three-dimensional structure that is retained upon implantation of said tissue into a mammal, and wherein the tissue is further comprised of post-mitotic cells, and wherein the protein is produced sufficiently to provide a therapeutic effect to said mammal once the organized tissue is implanted into said mammal.

33. An organized tissue having a three-dimensional cellular organization of a tissue of interest that is retained upon implantation of said tissue into a mammal, said tissue producing a protein of a type or in an amount not normally produced by a tissue of interest, comprising:

a plurality of cells, wherein at least a subset of said cells comprise a foreign DNA sequence operably linked to a promoter and encoding a protein, wherein said tissue has a three-dimensional geometry approximating the in vivo gross morphology of said tissue of interest, and wherein the organized tissue is further comprised of post-mitotic cells, and;

wherein the protein is produced to detectable levels in said tissue.

34. An organized tissue attached to a surface of a substrate, said tissue producing a protein, comprising:

a plurality of cells, wherein at least a subset of said cells comprise a foreign DNA sequence operably linked to a promoter and encoding a protein, wherein said cells form an organized tissue having a three-dimensional geometry approximating the in vivo gross morphology of a tissue of interest, and wherein said organized tissue is attached to the surface of a substrate, and wherein the organized tissue is further comprised of post-mitotic cells, and;

wherein the protein is produced to detectable levels in said tissue.

35. The organized tissue of claim 34, said substrate being selected from the group consisting of metal or plastic.

36. The organized tissue of claim 35, said metal substrate being steel mesh having a longitudinal axis and first and second points for attachment, and wherein said first and second attachment sites of said tissue are attached, respectively, to said first and second points of attachment.

* * * * *